US010328212B2

(12) United States Patent
Bender et al.

(10) Patent No.: US 10,328,212 B2
(45) Date of Patent: Jun. 25, 2019

(54) SINGLE SLIDER DOUBLE BARREL SYRINGE AND METHOD TO USE SAME FOR MEDICAL DIAGNOSTICS, THERAPEUTIC USE, AND PLACEMENT CONFIRMATION AND JOINT SPACE INJECTION

(71) Applicant: Accuro Technologies Inc., Victoria (CA)

(72) Inventors: Adam Bender, Qualicum Beach (CA); Michael Dolphin, Victoria (CA)

(73) Assignee: Accuro Technologies Inc., Victoria (CA)

( * ) Notice: Subject to any disclaimer, the term of this patent is extended or adjusted under 35 U.S.C. 154(b) by 10 days.

(21) Appl. No.: 15/491,730

(22) Filed: Apr. 19, 2017

(65) Prior Publication Data

US 2017/0304553 A1 Oct. 26, 2017

Related U.S. Application Data

(60) Provisional application No. 62/401,618, filed on Sep. 29, 2016, provisional application No. 62/326,597, filed on Apr. 22, 2016.

(51) Int. Cl.
*A61M 5/19* (2006.01)
*A61M 5/24* (2006.01)
(Continued)

(52) U.S. Cl.
CPC .......... *A61M 5/31576* (2013.01); *A61M 5/19* (2013.01); *A61M 5/31* (2013.01);
(Continued)

(58) Field of Classification Search
CPC ........ A61M 5/3129; A61M 2005/3128; A61M 5/31; A61M 5/31576; A61M 5/31511; A61M 2005/312; A61M 2005/3104
See application file for complete search history.

(56) References Cited

U.S. PATENT DOCUMENTS 2,496,559 A 2/1950 Piechaczek
3,678,959 A * 7/1972 Liposky .............. A61M 39/223
137/625.11
(Continued)

FOREIGN PATENT DOCUMENTS

DE 40 39 522 C1 4/1992
EP 0 210 160 A1 1/1987
(Continued)

OTHER PUBLICATIONS

Cajori et al., "The chemical composition of synovial fluid in cases of joint effusion", Journal of biological chemistry, 76, 471-480. 1928.
(Continued)

*Primary Examiner* — Theodore J Stigell
(74) *Attorney, Agent, or Firm* — Seed Intellectual Property Law Group LLP

(57) ABSTRACT

A syringe is provided having a hub with an orifice, first and second barrels having interior surfaces to form respective lumens, a slider, and an optional test indicator. The first and second barrels slideably receive respective first and second plungers for movement therein. The slider is operable to provide a fluidly communicative path between the orifice of the hub and the first and second barrel lumens. The optional test indicator is responsive to at least one characteristic of bodily fluid, the test indicator positioned to be exposed to any bodily fluid drawn into the first barrel lumen and visible from an exterior of the first barrel.

37 Claims, 10 Drawing Sheets

(51) Int. Cl.
*A61M 5/31* (2006.01)
*A61B 10/00* (2006.01)
*A61M 39/22* (2006.01)
*A61M 39/24* (2006.01)
*A61M 5/315* (2006.01)

(52) U.S. Cl.
CPC ...... *A61M 5/3129* (2013.01); *A61M 5/31511* (2013.01); *A61M 39/223* (2013.01); *A61B 10/0045* (2013.01); *A61M 2005/2407* (2013.01); *A61M 2005/312* (2013.01); *A61M 2005/3104* (2013.01); *A61M 2005/3128* (2013.01); *A61M 2039/224* (2013.01); *A61M 2039/242* (2013.01); *A61M 2205/13* (2013.01); *A61M 2205/583* (2013.01); *A61M 2205/584* (2013.01); *A61M 2210/08* (2013.01)

(56) References Cited

U.S. PATENT DOCUMENTS

| | | |
|---|---|---|
| 3,749,084 A | 7/1973 | Cucchiara |
| 4,044,757 A | 8/1977 | McWhorter et al. |
| 4,610,666 A * | 9/1986 | Pizzino ............... A61M 5/19 604/191 |
| 4,979,942 A | 12/1990 | Wolf et al. |
| 5,339,829 A | 8/1994 | Thieme et al. |
| 5,944,054 A * | 8/1999 | Saieva ............... A62B 9/02 128/201.28 |
| 6,126,644 A | 10/2000 | Naganuma et al. |
| 2008/0167621 A1 | 7/2008 | Wagner et al. |
| 2009/0104714 A1 | 4/2009 | Thomas et al. |
| 2009/0198182 A1 | 8/2009 | Fujishima et al. |
| 2009/0198211 A1 | 8/2009 | Thorne, Jr. et al. |
| 2010/0106097 A1 | 4/2010 | Elmouelhi |
| 2011/0118659 A1 | 5/2011 | Maaskamp et al. |
| 2014/0261082 A1 | 9/2014 | Anderson et al. |
| 2015/0112248 A1 | 4/2015 | Helliwell et al. |

FOREIGN PATENT DOCUMENTS

| | | |
|---|---|---|
| EP | 0 312 394 A2 | 4/1989 |
| WO | 1997/006428 A1 | 2/1997 |
| WO | 01/97881 A1 | 12/2001 |
| WO | 2007/035621 A1 | 3/2007 |
| WO | 2007/149980 A2 | 12/2007 |
| WO | 2012/139035 A1 | 10/2012 |
| WO | 2017/120358 A1 | 7/2017 |

OTHER PUBLICATIONS

Omar et al., "Preliminary results of a new test for rapid diagnosis of septic arthritis with use of leukocyte esterase and glucose reagent strips", The Journal of Bone and Joint Surgery, 96, 2032-2037. 2014.

* cited by examiner

SINGLE SLIDER DOUBLE BARREL SYRINGE AND METHOD TO USE SAME FOR MEDICAL DIAGNOSTICS, THERAPEUTIC USE, AND PLACEMENT CONFIRMATION AND JOINT SPACE INJECTION

BACKGROUND

Technical Field

The present disclosure generally relates to syringes.

Description of the Related Art

Patients suffering from acute or chronic pain in their joints typically receive injections in the joint space for relief and therapeutic purposes. These injections are commonly known as intra-articular injections. Intra-articular injections are typically administered by orthopedic surgeons, rheumatologists, and other physicians and health care professionals.

Intra-articular injections typically include therapeutics that assist in pain relief or treatment by administration thereof into the affected areas. In some instances, intra-articular injection therapeutics may be in the form of steroids. Such steroids may have anti-inflammatory properties that can decrease inflammation of the affected joint; provide relief to patients with non-inflammatory arthritis, such as osteoarthritis; or protect joint cartilage. In other instances, the intra-articular injection therapeutics may have properties that improve the lubrication of the joint, reduce pain, or improve range of motion. Still further, in other instances, the intra-articular injection therapeutics may include local anesthetic to provide a temporary analgesic affect.

Administering Intra-articular injections, however, is a complicated procedure, which requires precise positioning. A substantial portion of intra-articular injections are not effectively administered because of the complex human anatomy and precise positioning required to inject the therapeutic into the joint space. This often results in physicians and professionals using expensive, time-consuming, and complex medical imaging tools to properly administer intra-articular injection in the three-dimensional structure of a patient's joint space. Even using medical imaging tools, the physician may miss the precise location, thus failing to deliver effective treatment.

Commercial implementation of such intra-articular injections may include using a delivery device, such as a syringe, for example. Exemplary implementations of such delivery devices are shown and described in the present assignee's commonly owned U.S. patent application Ser. Nos. 14/519,934 and 62/275,422, which are incorporated herein by reference in their entireties.

To effectively administer such intra-articular injections in a simplified manner, reducing the number of components in the delivery device can improve manufacturing and labor costs. Further, reducing the number of components, in particular, moving components, and improving sealability of syringe chambers which house various fluids can avoid, limit, or mitigate cross-contamination between, for example, adjacent barrels of the syringe. Still further, reducing the number of components, in particular, moving components, can avoid, limit, or mitigate the number of parts that can malfunction and lead to cross-contamination. Consequently, new approaches to administration of intra-articular injections that reduce the number of components used in the delivery device are highly desirable.

BRIEF SUMMARY

In various implementations, syringes with robust and efficient form factors enable precise placement of a needle tip and sterile administration of intra-articular injections in joint spaces. The syringes can include a single slider or a single valve, which enables users, such as physicians, to effectively test for precise positioning of a needle tip in joint spaces and administer intra-articular injections in a simplified manner. For example, the various implementations of the syringes disclosed herein include a single slider that can translate between at least two positions, which can allow the user to withdraw fluids from patients to determine precise location and thereafter administer intra-articular injections. Furthermore, in contrast to having two or more valves to control the withdrawal and injection configurations, the various implementations of the syringes disclosed having the single slider that moves between the withdrawal and injection configurations can reduce complexity as well as manufacturing and labor costs. Still further, having a syringe with a single slider can mitigate, limit, or avoid having multiple moveable parts that can malfunction and lead to cross-contamination and other types of catastrophic failure.

Moreover, in contrast to syringes which include rotatably-moveable switching devices to alternate between withdrawal and injection positions, such as stop-cocks for example, the various implementations of the syringes disclosed herein slideably translate between various positions. Such slideable translation can advantageously reduce or mitigate needle tip movement during the switching. Further, such slideable translation can improve efficiencies and avoid or limit delays in confirming alignment of rotatably-moveable components by users through easy and simple translation movements of the slider. For instance, some implementations of the syringes disclosed herein can include stops at opposing ends of the sliders which can confirm the positioning of the slider in withdrawal or injection positions.

Further, the various implementations of the syringes disclosed herein are capable of withstanding high pressure loading while limiting, mitigating, or preventing leaks within the various chambers of the syringes. For example, the various implementations of the syringes disclosed herein include sliders having seal devices, such as O-rings, for example, which are disposed around the sliders and coupled thereto. In this manner, the seal devices are capable of translating with the slider, which limits, restricts, or mitigates fluctuations in size, shape, etc. of the sealed chambers of the syringe, and can therefore also omit including apertures or other features required for venting in the syringe. Further, the seal devices can be positioned around the sliders such that when high pressures are applied, for example, the increase in pressure can act equally on the slider with zero net force. The increase in chamber pressures capabilities of the disclosed implementations of the syringes can allow the seal devices to expand or move, further improving the sealing capability of the syringes.

Still further, the various implementations of the syringes disclosed herein can simplify and reduce the forces required to switch the syringe between various positions while improving the sealing capability. For instance, positioning the seal devices in the various manners described herein can allow seal devices to be maintained with low frictional sealing forces between the seal devices and a communal hub which houses the sliders. Consequently, the various sliders disclosed herein can move with ease due, in part, to low static friction forces and lower pre-compression of the seal devices.

An exemplary implementation of a syringe can be summarized as including a first barrel having an interior surface that forms a first barrel lumen, a second barrel having an interior surface that forms a second barrel lumen, a hub, and a slider. The first barrel can include a first plunger having a head, the head of the first plunger slideably received in the first barrel lumen for movement therein, where the head of the first plunger is in sealing engagement with the interior surface of the first barrel. The second barrel can include a second plunger having a head, the head of the second plunger slideably received in the second barrel lumen for movement therein, where the head of the second plunger is in sealing engagement with the interior surface of the second barrel. The hub can have an orifice, where the hub provides a first fluidly communicative path between the orifice of the hub and the first barrel lumen and a second fluidly communicative path between the orifice of the hub and the second barrel lumen, at least a portion of the first and the second fluidly communicative paths extending parallel to one another.

The slider is slideably received via the hub and translatable along an axis that is perpendicular to at least the portions of the first and the second fluidly communicative paths which extend parallel to one another, between a first configuration and a second configuration. The slider in the first configuration opens the first fluidly communicative path between the orifice of the hub and the first barrel lumen and closes the second fluidly communicative path between the orifice of the hub and the second barrel lumen, and the slider in the second configuration opens the second fluidly communicative path between the orifice of the hub and the second barrel lumen and closes the first fluidly communicative path between the orifice of the hub and the first barrel lumen. In some implementations, the syringe can also include a test indicator responsive to at least one characteristic of the bodily fluid, the test indicator positioned to be exposed to any bodily fluid drawn into the first barrel lumen and visible from an exterior of the first barrel.

Another exemplary implementation of a syringe can be summarized as including a first barrel having an interior surface that forms a first barrel lumen which receives bodily fluid, a second barrel having an interior surface that forms a second barrel lumen which holds an injectable fluid, a hub, and a slider. The first barrel can include a first plunger having a head, the head of the first plunger slideably received in the first barrel lumen for movement therein, where the head of the first plunger is in sealing engagement with the interior surface of the first barrel. The second barrel can include a second plunger having a head, the head of the second plunger slideably received in the second barrel lumen for movement therein, where the head of the second plunger is in sealing engagement with the interior surface of the second barrel. The hub can have an orifice through which bodily fluid is drawn into the first barrel lumen and the injectable fluid is expelled from the second barrel lumen.

The slider can include an exterior surface, where the slider translates between a first position and a second position in a direction which is perpendicular to a flow path of the bodily fluid drawn into the hub, the exterior surface of the slider exposed to the bodily fluid when the bodily fluid is drawn into the hub and the exterior surface of the slider exposed to the injectable fluid when the injectable fluid is expelled from the hub. The slider in the first position opens a fluidly communicative path between the orifice of the hub and the first barrel lumen and closes a fluidly communicative path between the orifice of the hub and the second barrel lumen. The slider in the second position opens a fluidly communicative path between the orifice of the hub and the second barrel lumen and closes the fluidly communicative path between the orifice of the hub and the first barrel lumen. In some implementations, the syringe can also include a test indicator responsive to at least one characteristic of the bodily fluid, the test indicator positioned to be exposed to any bodily fluid drawn into the first barrel lumen and visible from an exterior of the first barrel.

An exemplary implementation of a method for administering intra-articular injections via a syringe which includes a first barrel having a first barrel lumen, a second barrel having a second barrel lumen, a common hub, a needle coupled to the common hub, a slider moveable between first and second positions which fluidly communicatively couples the common hub with the first and the second barrel lumens, and at least one test indicator disposed in a test indicator housing coupled to the first barrel can be summarized as including, in response to a lateral translation of a slider to the first position, opening a first fluidly communicative path between an orifice and an interior of the first barrel and closing a second fluidly communicative path between the orifice and an interior of the second barrel. The method can include receiving bodily fluid into the first barrel lumen via the needle when the slider is in the first position, exposing the test indicator to the bodily fluid, and producing a defined visual indication by the test indicator. The method can include, in response to a lateral translation of a slider to the second position, opening the second fluidly communicative path between the orifice and the interior of the second barrel and closing the first fluidly communicative path between the orifice and the interior of the first barrel, and expelling a fluid from the second barrel via the orifice and the needle.

DETAILED DESCRIPTION

Figure 1:
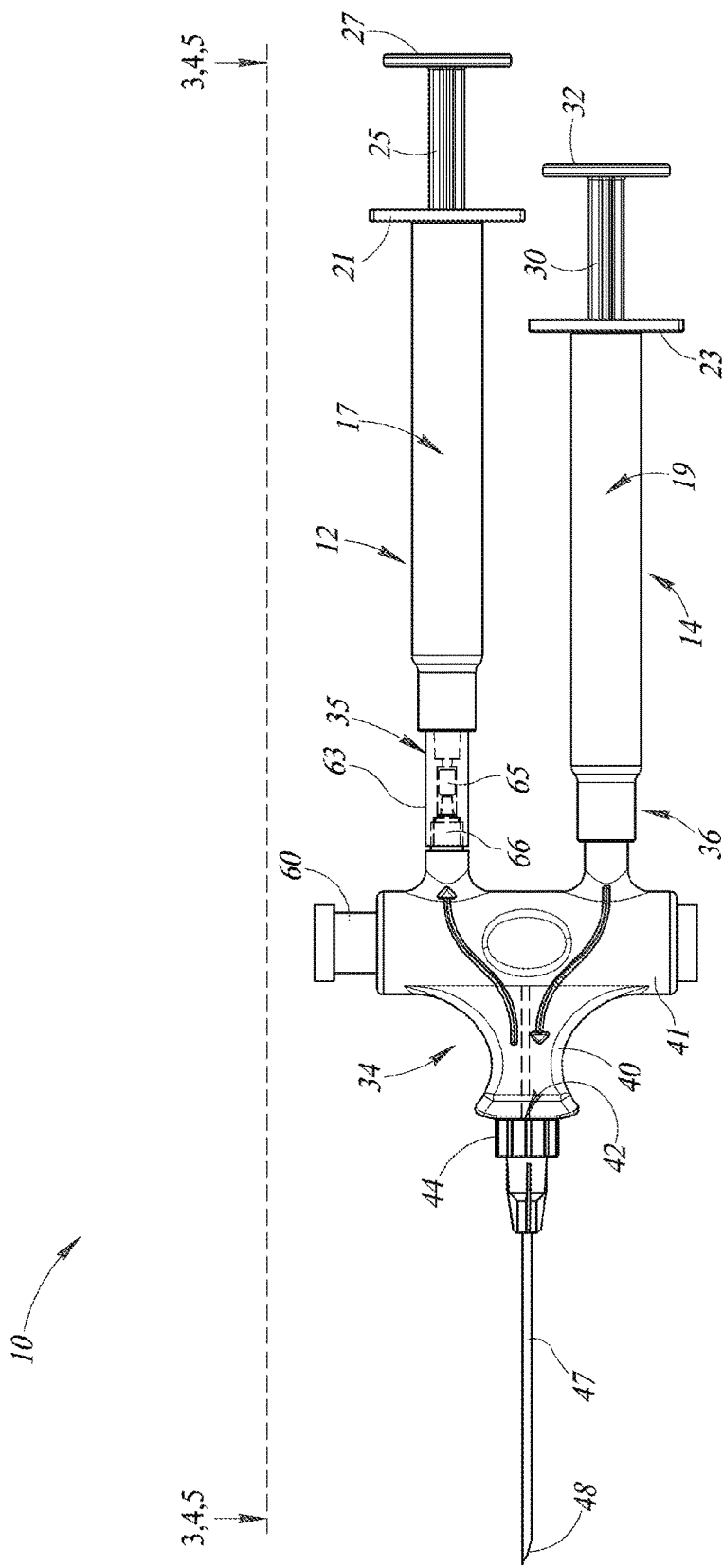
FIG. 1 is a plan view of a syringe, according to one implementation.
Figure 2:
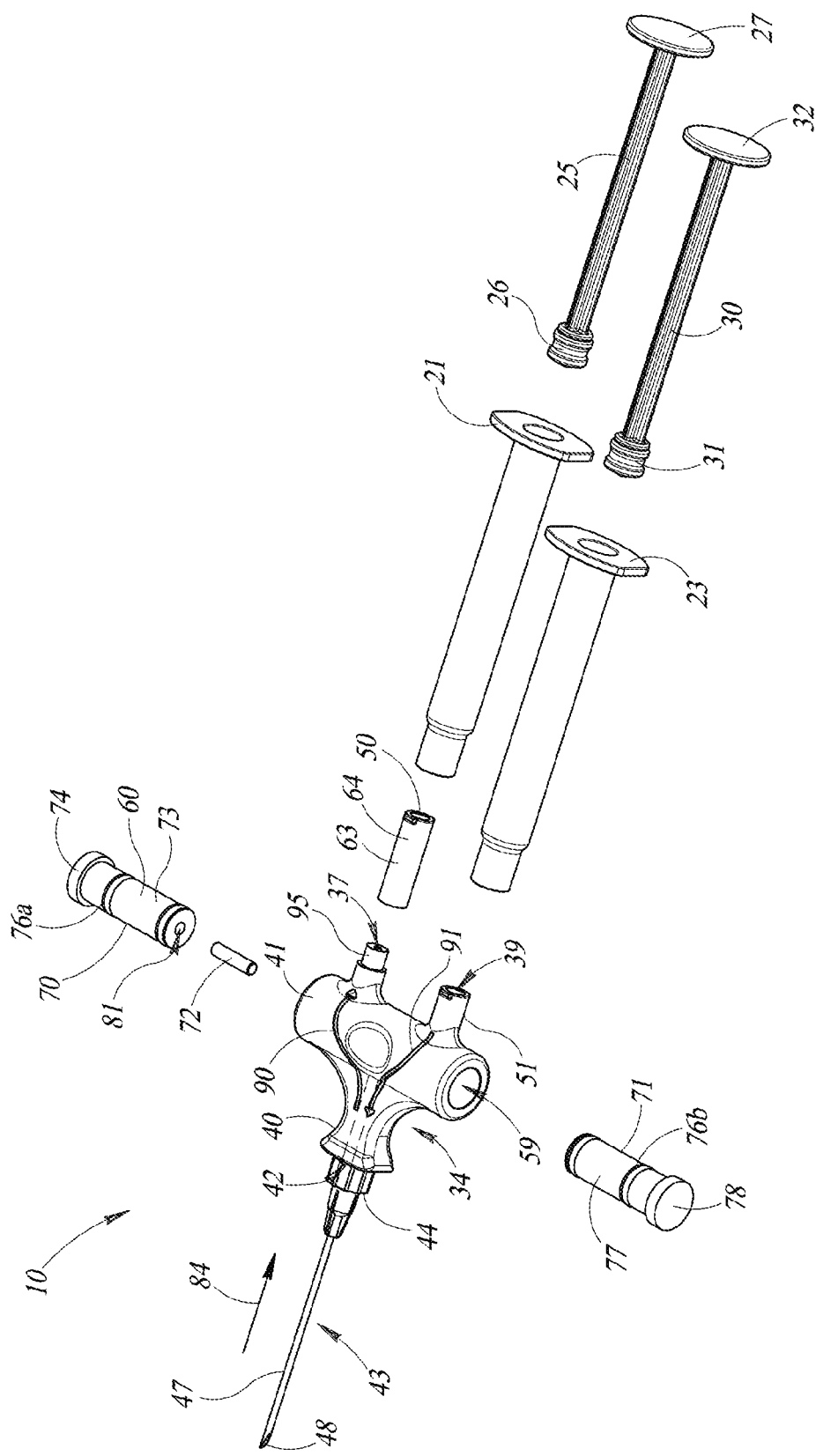
FIG. 2 is an exploded view of the syringe of FIG. 1.

In the following description, certain specific details are set forth in order to provide a thorough understanding of various disclosed implementations. However, one skilled in the relevant art will recognize that implementations may be practiced without one or more of these specific details, or with other methods, components, materials, etc. In other instances, well-known structures associated with syringes and related syringe assemblies have not been shown or described in detail to avoid unnecessarily obscuring descriptions of the implementations.

Unless the context requires otherwise, throughout the specification and claims which follow, the word "comprise" and variations thereof, such as "comprises" and "comprising," are to be construed in an open, inclusive sense that is as "including, but not limited to."

Reference throughout this specification to "one implementation" or "an implementation" means that a particular feature, structure or characteristic described in connection with the implementation is included in at least one implementation. Thus, the appearances of the phrases "in one implementation" or "in an implementation" in various places throughout this specification are not necessarily all referring to the same implementation. Furthermore, the particular features, structures, or characteristics may be combined in any suitable manner in one or more implementations.

FIGS. 1 through 5B illustrate a syringe 10, according to one example implementation. The syringe 10 may, for example, be used to provide intra-articular injections. For example, the syringe 10 may be used to determine where a needle tip is currently positioned within a three-dimensional structure of a joint and to deliver an injectable fluid to a desired location, such as an intra-articular location. In some implementations, the syringe 10 may be used to apply injections in an intrathecal space where fluid withdrawal may be required and precise positioning of the needle tip to deliver an injectable fluid may also be required. In some implementations, the syringe 10 may be used to implement complex procedures where minimal movement of the syringe 10 may be required along with fluid withdrawal and delivery of an injectable fluid, such as ophthalmic injections, intracerebral injections, and otolaryngological procedures. The injectable fluid may include a therapeutic agent (e.g., an Active Pharmaceutical Agent, such as corticosteroid, hyaluronic acid or a biologic). Alternatively, the injectable fluid may include a diagnostic agent, such as X-ray-contrast preparations, radioactive isotopes, and/or dyes. In some implementations, the injectable fluid may include a combination of a therapeutic agent and a diagnostic agent. The injectable fluid may further include excipients or other pharmaceutically inactive substances formulated with the therapeutic agent and/or diagnostic agents.

The syringe 10 includes a withdrawal chamber barrel 12 and an injectable fluid chamber barrel 14. The barrels 12, 14 each have a respective interior space or lumen 17, 19. The withdrawal chamber barrel 12 and the injectable fluid chamber barrel 14 may be formed of transparent or translucent materials, such as clear plastic or glass, to allow a user to view the interior of the withdrawal chamber and injectable fluid chamber barrels 12, 14. In addition, the withdrawal chamber and injectable fluid chamber barrels 12, 14 may include graduation markings to allow the user to view a fluid against the graduation markings to assess the volume of fluid in the respective chamber barrels 12, 14.

An upper end of the withdrawal chamber barrel 12 optionally includes a finger flange 21 that extends peripherally around an upper end of the withdrawal chamber barrel 12. In some implementations, including the implementation shown in FIGS. 1 through 5B, the finger flange 21 of the withdrawal chamber barrel 12 has a substantially rectangular shape. In other implementations, the finger flange 21 may have any other shape, such as cylindrical, hexagonal, square, oval, etc. The finger flange 21 assists a user by providing a gripping surface during use.

An upper end of the injectable fluid chamber barrel 14 optionally includes a finger flange 23 that extends peripherally around an upper end of the injectable fluid chamber barrel 14. In some implementations, as illustrated in FIGS. 1 through 5B, the finger flange 23 of the injectable fluid chamber barrel 14 has a substantially rectangular shape. In other implementations, the finger flange 23 may have any other shape, such as circular, hexagonal, square, oval, etc. The finger flange 23 also assists a user by providing a gripping surface during use.

The syringe 10 includes a first plunger 25 and a head or plunger seal 26 at a lower end of the first plunger 25. The first plunger 25 is partially received in the withdrawal chamber lumen 17 of the withdrawal chamber barrel 12. The plunger seal 26 sealingly engages with an interior surface of the withdrawal chamber barrel 12 which forms the withdrawal chamber lumen 17. The first plunger 25 is slideably moveable within the withdrawal chamber barrel 12 and includes a thumb rest 27. The sealing engagement of the plunger seal 26 with the interior surface of the withdrawal chamber barrel 12 creates a vacuum in the withdrawal chamber barrel lumen 17 in response to movement of the first plunger 25. The vacuum created in the withdrawal chamber barrel lumen 17 facilitates creating a pressure differential to draw fluid toward the withdrawal chamber barrel lumen 17 in response to distal movement of the first plunger 25. For instance, the withdrawal chamber barrel 12 can be coupled to a source of fluid, such as, for example, an intra-articular joint of a patient. Distal movement of the first plunger 25 relative to the lower end of the withdrawal chamber barrel 12 creates a negative relative pressure or vacuum in the withdrawal chamber lumen 17 to draw the fluid toward the withdrawal chamber lumen 17 from the source of fluid. The plunger seal 26 may, for instance, be made from rubber or a resilient, conformable polymer, such as an elastomer.

The syringe 10 also includes a second plunger 30 and a head or plunger seal 31 at a lower end of the second plunger 30. The second plunger 30 is partially received in the injectable fluid chamber lumen 19 of the injectable fluid chamber barrel 14. The plunger seal 31 sealingly engages with an interior surface of the injectable fluid chamber barrel 14 which forms the injectable fluid chamber lumen 19. The second plunger 30 is slideably moveable within the injectable fluid chamber barrel 14 and includes a thumb rest 32. The sealing engagement of the plunger seal 31 with the interior surface of the injectable fluid chamber barrel 14 creates a vacuum in the injectable fluid chamber barrel lumen 19 in response to movement of the second plunger 30. The vacuum created in the injectable fluid chamber barrel lumen 19 facilitates creating a pressure differential to draw fluid in the injectable fluid chamber lumen 19 in response to distal movement of the second plunger 30. For instance, the injectable fluid chamber barrel 14 can be coupled to a bottle, bolus, or other source of fluid to draw the injectable fluid, such as, for example, medicant(s) contained in the bottle. In alternate implementations, however, the injectable fluid can be pre-loaded in the injectable fluid chamber barrel 14 prior to delivery to a user, for example, a healthcare provider. Again, the medicant(s) can include a therapeutic agent (e.g., an Active Pharmaceutical Agent, such as corticosteroid, hyaluronic acid or a biologic). Alternatively, the injectable fluid may include a diagnostic agent, such as X-ray-contrast preparations, radioactive isotopes, and/or dyes. In some implementations, the injectable fluid can include a combination of a therapeutic agent and a diagnostic agent. The injectable fluid may further include excipients or other pharmaceutically inactive substances formulated with the therapeutic agent and/or diagnostic agents.

Distal movement of the second plunger 30 relative to the lower end of the injectable fluid chamber barrel 14 creates a negative relative pressure or vacuum in the injectable fluid chamber lumen 19 to draw the fluid in the injectable fluid chamber lumen 19 from the bottle or other source of fluid. Conversely, proximal movement of the second plunger 30 relative to the lower end of the injectable fluid chamber barrel 14 creates a positive pressure to expel the fluid in the injectable fluid chamber barrel lumen 19. Again, the plunger seal 31 may, for instance, be made from rubber or a resilient, conformable polymer, such as an elastomer.

The withdrawal chamber barrel 12 and the injectable fluid chamber barrel 14 are detachably coupleable to a communal hub 34. In particular, the syringe 10 includes coupling adapters 35, 36, for example, in the form of female and male Luer-Lock portions, which directly or indirectly couple the withdrawal chamber and the injectable fluid chamber barrels 12, 14 to the communal hub 34. Female couplers, for example, in the form of female Luer-Lock portions, are located at respective lower ends of the withdrawal chamber barrel 12 and the injectable fluid chamber barrel 14. Male coupler 51, for example, in the form of a male Luer-Lock portion, is located at a lower end of the communal hub 34 proximal to an injectable fluid chamber fluid port 39 which provides a fluidly communicative path to the injection chamber barrel lumen 19. Male coupler 50, for example, in the form of a male Luer-Lock portion is located at a lower end of a test indicator housing 63 which provides a fluidly communicative path to the withdrawal chamber barrel lumen 17. The male Luer-Lock portions are physically detachably coupleable to corresponding female Luer-Lock portions. In this manner, the withdrawal chamber barrel 12 and/or the injectable fluid chamber barrel 14 may each be selectively detachable from the syringe 10.

The communal hub 34 includes a needle portion 40 and a slider portion 41. The needle portion 40 includes one or more needle ports 42 through which a needle 43 is coupled to the communal hub 34. For example, the one or more needle ports 42 may be formed by or part of a Luer-Lock connector or coupler. For example, the needle port 42 may be part of a male Luer-Lock portion and the needle 43 may include a female Luer-Lock portion that detachably rotatingly couples with the male Luer-Lock portion. While the implementation illustrated in FIGS. 1 through 5B includes a Luer-Lock connection, in other implementations, the communal hub 34 may include a slip-tip, an eccentric tip, or other types of needle adapters to couple the communal hub 34 to the needle 43. Still further, in some implementations, the coupler or connector that forms a Luer-Lock connection may be integrally formed with the communal hub 34 as a unitary, single piece.

The needle 43 includes a needle hub 44 and a needle shaft 47. Again, in some implementations, the needle hub 44 may be integrally formed with the communal hub 34 as a unitary, single piece. The needle shaft 47 includes a beveled end or point or tip 48, and includes a lumen extending therethrough. The needle 43 is fluidly communicatively coupled to the syringe 10 to withdraw or expel fluid when administering to a patient.

The slider portion 41 of the communal hub 34 is substantially cylindrical shaped and hollow, and defines an opening 59 to receive a slider 60, as discussed in more detail below. The slider portion 41 includes a first port 61 in fluid communication with the needle port 42 and the withdrawal chamber fluid port 37 disposed in the connector 95 and the injectable fluid chamber fluid port 39 disposed in the male coupler 51. As discussed above, the male coupler 51 is sized and shaped to couple to or with the injectable fluid chamber barrel 14. As discussed above, at one end, the male coupler 50 couples the test indicator housing 63 to or with the withdrawal chamber barrel 12. At another end, the test indicator housing 63 is sized and shaped to couple to or with the communal hub 34. In some implementations, the communal hub 34 includes the connector 95 which can couple to or with the test indicator housing 63 via welded structures, snap fit structures, adhesives, or other suitable connecting structures. Again, in some implementations, the test indicator housing 63 can be coupled to the communal hub 34 and the withdrawal chamber barrel 12 via Luer-Lock couplers or connectors.

The test indicator housing 63 is substantially cylindrical shaped and hollow to define a test indicator chamber 64. The test indicator chamber 64 is sized and shaped to house a test indicator 65 and a one-way valve 66. The test indicator 65 typically provides a visual indication (e.g., appearance of line, change of color) when contacted by a defined substance. In particular, the test indicator 65 is located in the test indicator chamber 64 so as to be contacted by fluid drawn into the withdrawal chamber lumen 17 via operation of the first plunger 25. As illustrated in FIGS. 1 through 5B, the test indicator 65 may take the form of a test strip that is removably received in the test indicator chamber 64. The test indicator 65 can take the form of a cylindrical shaped test strip, rectangular shaped test strip, or any other shape or form of test strip which is formed of material (e.g., lateral flow strip) with one or more substances (e.g., reagents) that react in a defined manner (e.g., change color) in the presence of defined substances (e.g., protein, glucose, etc.).

The one-way valve 66 is disposed in the test indicator chamber 64 and is fluidly coupled to the withdrawal chamber fluid port 37. The one-way valve 66 allows flow of fluids in one direction, i.e., into the withdrawal chamber barrel 12, and prevents flow of fluids out of the withdrawal chamber barrel 12 into the opening 59, or internal pathways beneath the one-way valve 66. In this manner, the one-way valve 66 can prevent and/or avoid any cross-contamination of fluids flowing out of the withdrawal chamber barrel 12 and flowing into the injection chamber barrel 14. The one-way valve 66 may be duckbill valves, check valves, ball valves, butterfly valves, cross-slit valves, umbrella valves, or the like. By way of example, the illustrated embodiment of FIGS. 1-5B includes a check valve that is positioned in the test indicator chamber 64.

As discussed above, the slider portion 41 of the communal hub 34 includes the opening 59 to receive the slider 60. The slider 60 includes a first portion 70, a second portion 71, and a pin 72, or other suitable alignment structures. In some implementations, for example as illustrated in FIGS. 1-5B, the slider 60 includes separate first portion 70 and second portion 71 which are coupled together to facilitate ease of assembly and manufacturing. For instance, the first portion 70 is received through the opening 59 from one end of the opening 59 while the second portion 71 is received through the opening 59 from the other end of the opening 59. After the first portion 70 and the second portion 71 are received in the opening 59, the first portion 70 is coupled to the second portion 71. For example, in some implementations, the first portion 70 and the second portion 71 can be coupled to each other via a snap fit structure, adhesive, ultrasonic welding, or other suitable coupling structures.

The first portion 70 includes a shaft portion 73 and a cap portion 74 extending from one end of the shaft portion 73.

The shaft portion 73 includes at least a pair of slider grooves 75 which extend around a periphery of an outer surface of the shaft portion 73. The slider grooves 75 are sized and shaped to receive seal devices 76a, such as, for example, O-rings. The seal devices 76a are sized and shaped to provide a frictional fit between the first portion 70 and an interior surface of the slider portion 41 of the communal hub 34. Such frictional forces will at least be higher than the gravitational forces which will prevent the slider 60 from translating due to gravitational forces. Thus, in order to move or translate the slider, a user may depress the cap portion 74 with a force sufficient to overcome the frictional forces provided by the sealing engagement of the seal devices 76a with the interior surface of the slider portion 41.

As discussed above, the slider 60 is disposed in the opening 59 of the communal hub 34. More particularly, the shaft portion 73 of the first portion 70 is sized and shaped to define a relatively small gap D between an outer surface of the shaft portion 73 and an interior surface of the slider portion 41. In some implementations, the gap D may have a range of between 100 to 500 microns. In other implementations, the gap D may be sized to provide sufficient area to allow fluid flow while minimizing fluid losses to improve efficiency. In particular, the gap D defines a flow path for the fluid drawn into the communal hub 34 to flow around the outer surface of the shaft portion 73 to the withdrawal chamber barrel lumen 17.

Figure 3:
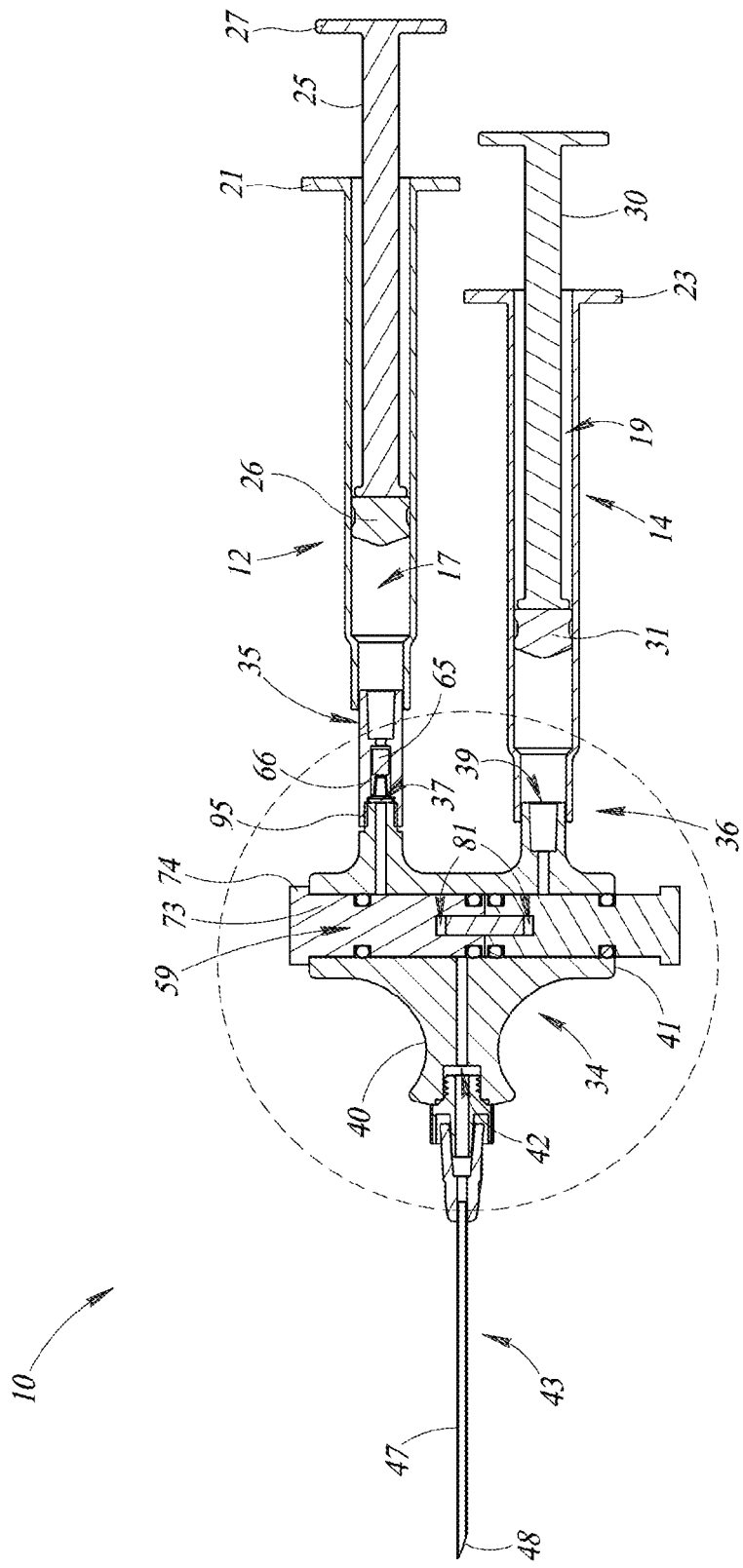
FIG. 3 is a cross-sectional view of the syringe of FIG. 1 taken along lines 3-3, illustrating the syringe in a withdrawal configuration.
Figure 3A:
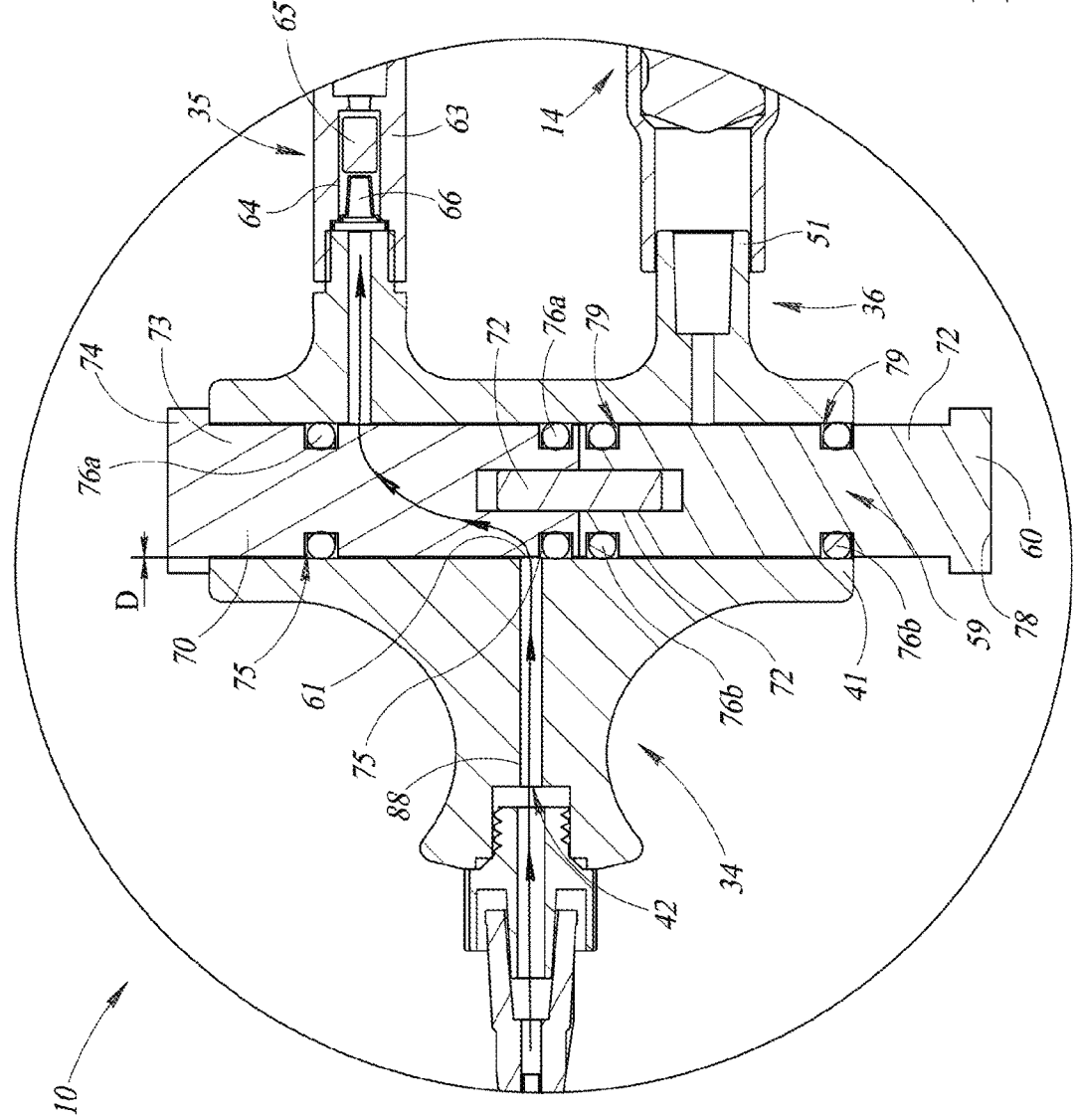
FIG. 3A is a detail view of the syringe of FIG. 1, illustrating a slider disposed in a hub in a withdrawal position.

The cap portion 74 of the first portion 70 is sized and shaped to have an external outer diameter which is greater than the outer diameter of the shaft portion 73. In particular, the cap portion 74 of the first portion 70 is sized and shaped to have an outer diameter which exceeds an outer diameter of the opening 59 disposed in the slider portion 41. In this manner, an inner surface of the cap portion 74 of the first portion 70 mates with an outer surface of the slider portion 41 to act as a stop when the slider 60 is received in the opening 59 and is in the first position (FIGS. 3 and 3A).

The second portion 71 also includes a shaft portion 77 and a cap portion 78 extending from one end of the shaft portion 77. The shaft portion 77 of the second portion 71 also includes at least a pair of slider grooves 79 which extend around a periphery of an outer surface of the shaft portion 77. The slider grooves 79 are sized and shaped to receive seal devices 76b, such as, for example, O-rings. Again, the seal devices 76b are sized and shaped to provide a frictional fit between the second portion 71 and the interior surface of the slider portion 41. Such frictional forces will at least be higher than the gravitational forces which will prevent the slider 60 from translating due to gravitational forces. Thus, in order to move or translate the slider 60, a user may depress the cap portion 78 with a force sufficient to overcome the frictional forces provided by the sealing engagement of the seal devices 76b with the interior surface of the slider portion 41.

As discussed above, the slider 60 is disposed in the opening 59 of the communal hub 34. More particularly, the shaft portion 77 of the second portion 71 is also sized and shaped to define a relatively small gap D between an outer surface of the shaft portion and an interior surface of the slider portion 41. The gap D defines a flow path for the fluid expelled from the injectable fluid chamber barrel 14 to flow around the outer surface of the shaft portion 77 to the first port 61.

The cap portion 78 of the second portion 71 is sized and shaped to have an external outer diameter which is greater than the outer diameter of the shaft portion 77. In particular, the cap portion 78 of the second portion 71 is sized and shaped to have an outer diameter which exceeds an outer diameter of the opening 59 disposed in the slider portion 41. In this manner, an inner surface of the cap portion 78 of the second portion 71 mates with an outer surface of the slider portion 41 to act as a stop when the slider 60 is received in the opening 59 and is in the second position (FIGS. 5 and 5A).

Both the first portion 70 and the second portion 71 include a respective pin opening 81 which partially extends through the respective shaft portions 73, 77. The pin openings 81 of the first portion 70 and the second portion 71 extend from ends which are opposite to ends which include the respective cap portions 74, 78. The pin openings 81 are sized and shaped to receive therein the pin 72. Thus, when the first portion 70 is coupled to the second portion 71, for example, the first and the second portions 70, 71 can slideably move along a longitudinal axis of the pin 72.

Figure 4:
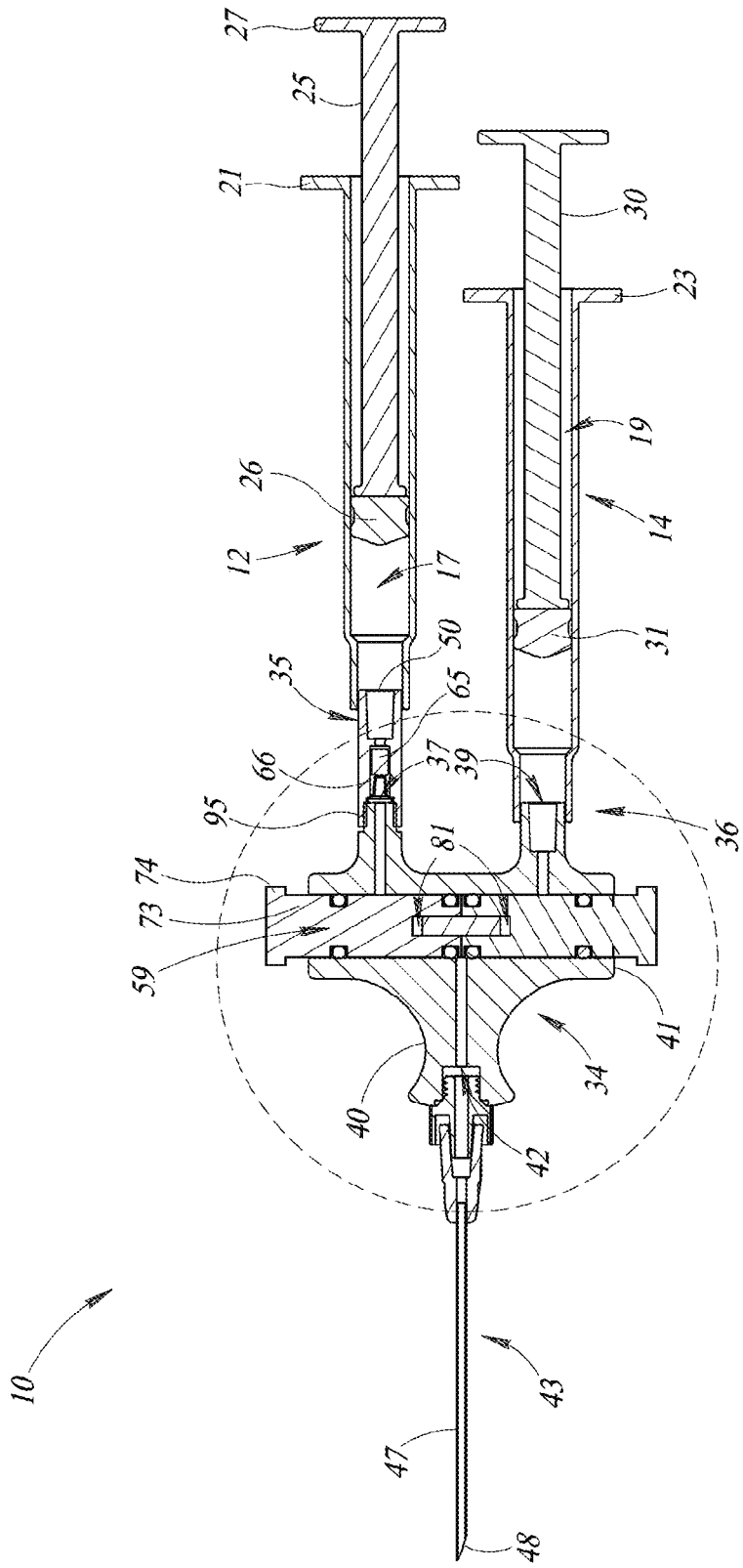
FIG. 4 is a cross-sectional view of the syringe of FIG. 1 taken along lines 4-4, illustrating the syringe in a neutral configuration.
Figure 4A:
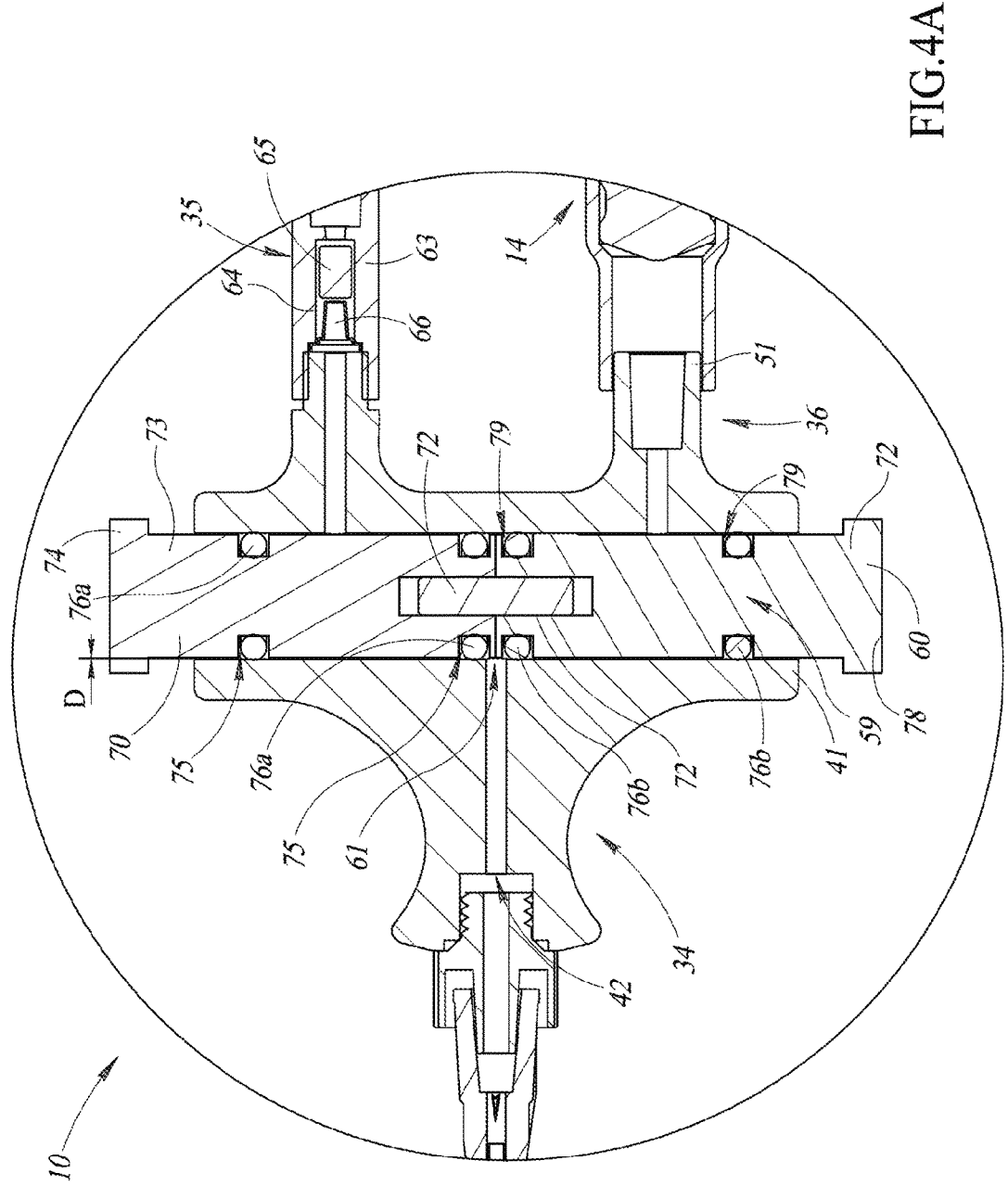
FIG. 4A is a detail view of the syringe of FIG. 1, illustrating a slider disposed in a hub in a neutral position.
Figure 5:
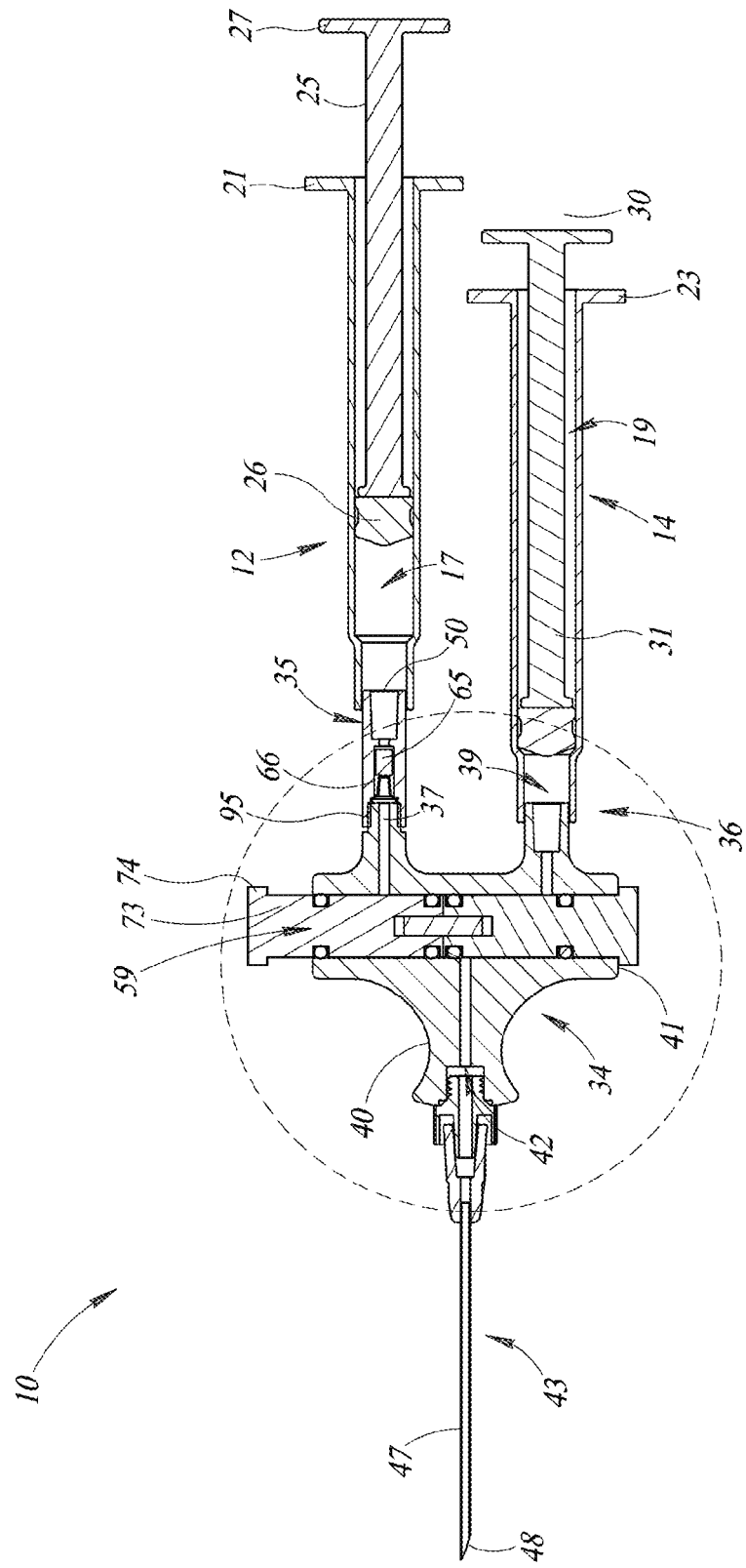
FIG. 5 is a cross-sectional view of the syringe of FIG. 1 taken along lines 5-5, illustrating the syringe in an injection configuration.
Figure 5A:
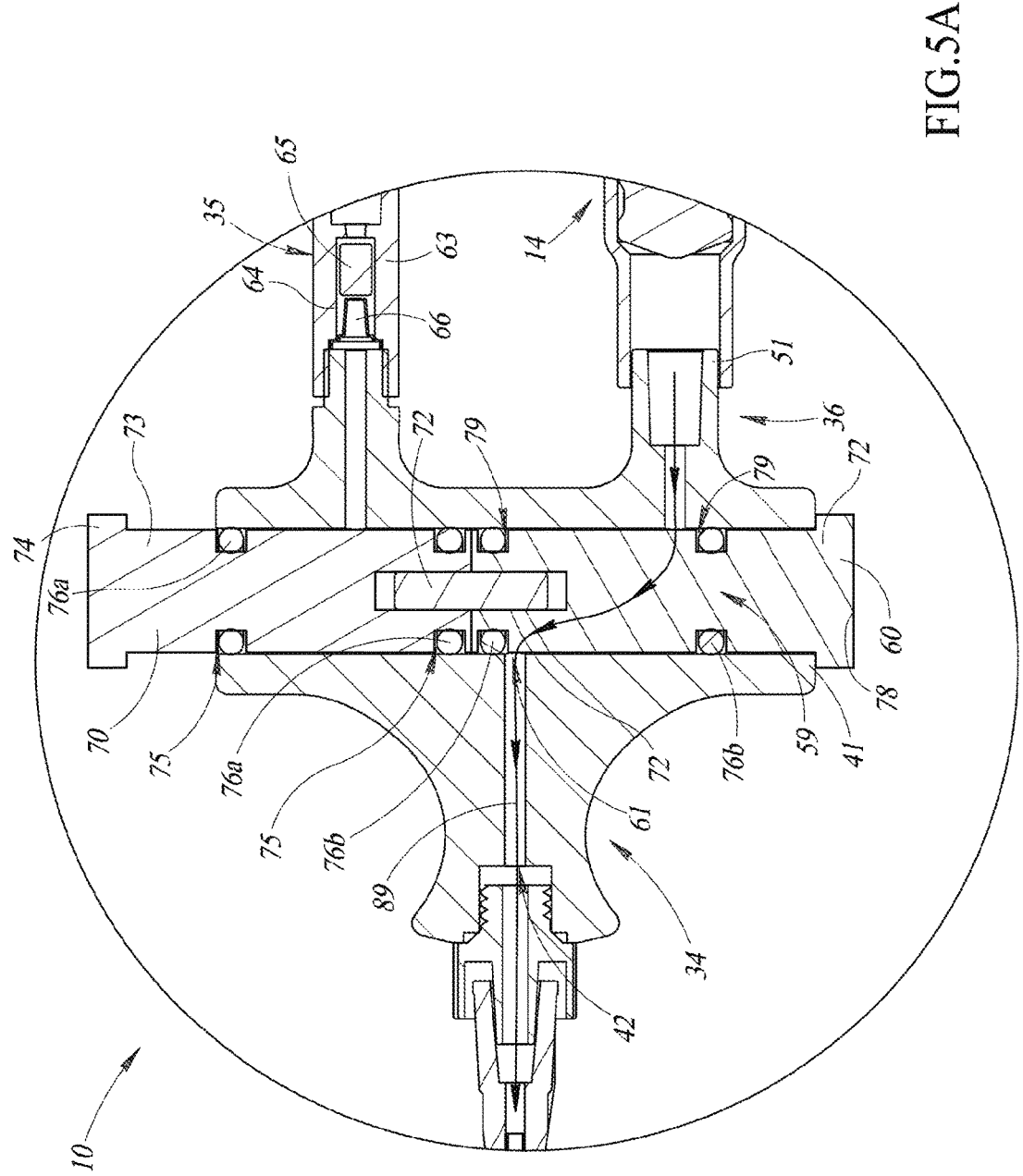
FIG. 5A is a detail view of the syringe of FIG. 1, illustrating a slider disposed in the hub in an injection position.

FIGS. 3-5B illustrate the syringe 10 in various configurations. The syringe 10 can be in a testing, withdrawing, or withdrawal configuration (FIGS. 3 and 3A), a neutral configuration (FIGS. 4 and 4A), and an injection configuration (FIGS. 5 and 5A). The slider 60 can translate between a withdrawal position which allows flow of fluid into the withdrawal chamber barrel lumen 17 and prevents flow of fluid in or out of the injection chamber barrel lumen 19, a neutral position which prevents flow of fluid from or into the withdrawal chamber barrel lumen 17 and the injection chamber barrel lumen 19, and an injection position which allows flow out of the injection chamber barrel lumen 19 and prevents flow of fluid into or out of the withdrawal chamber barrel lumen 17. More particularly, the slider 60 is disposed in the opening 59 of the communal hub 34 to translate between the different positions, e.g., withdrawal, neutral, and/or injection positions, in a direction which is substantially perpendicular to a flow path of fluid drawn into the communal hub 34 via the needle 43 and expelled from the communal hub 34 via the needle 43, as indicated by arrow 84. Similarly, the direction of translation of the slider 60 may also be perpendicular to flow paths of fluid in the withdrawal chamber barrel lumen 17 and out of the injection chamber barrel lumen 19.

In particular, FIGS. 3 and 3A illustrate the syringe 10 in a withdrawal configuration and, more specifically, FIG. 3A illustrates a detail view of the communal hub 34 and the slider 60, with certain components removed for clarity of description and illustration. As illustrated in FIGS. 3 and 3A, in the withdrawal configuration, the slider 60 is in the withdrawal position, where the inner surface of the cap portion 74 of the first portion 70 abuts or mates with the outer surface of the slider portion 41. When the slider 60 is in the withdrawal position, the seal devices 76a in the first portion 70 of the slider 60 are positioned to open a flow path from the needle port 42 disposed in the communal hub 34 to the withdrawal chamber fluid port 37 as indicated by arrow 88, while the seal devices 76b in the second portion 71 of the slider 60 are positioned to block a flow path from the needle port 42 disposed in the communal hub 34 to the injectable fluid chamber fluid port 39. For example, as the fluid flows around the slider 60 in the gap D, the seal devices 76a prevent the flow from traversing into the second portion 71 of the slider 60. In this manner, a user can draw fluid from joint spaces, such as fluids found in joints of a body, for example, synovial fluid. Synovial fluids have a high concentration of protein. Thus, to test such presence, the user may withdraw the first plunger 25 to withdraw fluid, e.g., fluid found in joint spaces, and receive at least some of such fluid in the withdrawal chamber barrel lumen 17. As noted above, however, other applications, such as, for example, injections into an intrathecal space, ophthalmic injections, intracerebral injections, and otolaryngological procedures are also within the scope of the disclosed subject matter.

More particularly, as the user withdraws the first plunger 25, the pressure differential created in the withdrawal chamber barrel lumen 17 and the communal hub 34—in particular, the negative relative pressure or vacuum in the withdrawal chamber barrel lumen 17—draws fluid toward the withdrawal chamber barrel lumen 17 and into the test indicator chamber 64, which exposes the test indicator 65 to the fluid.

FIGS. 4 and 4A illustrate the syringe 10 in a neutral configuration and, more specifically, FIG. 4A illustrates a detail view of the communal hub 34 and the slider 60, with certain components removed for clarity of description and illustration. As illustrated in FIGS. 4 and 4A, in the neutral configuration, the slider 60 is in a transition position relatively between the withdrawal and injection positions (FIGS. 3, 3A, 5, 5A). When the slider 60 is in the neutral position, the seal devices 76a in the first portion 70 of the slider 60 and the seal devices 76b in the second portion 71 of the slider 60 are positioned to block a flow path from the needle port 42 disposed in the communal hub 34 to the withdrawal chamber fluid port 37 and the flow path from the needle port 42 disposed in the communal hub 34 to the injectable fluid chamber port 39. In this manner, when the syringe 10 is in the neutral configuration, fluid may not flow into or out of the injection barrel lumen 19 and the withdrawal chamber barrel lumen 17.

FIGS. 5 and 5A illustrate the syringe 10 in an injection configuration and, more specifically, FIG. 5A illustrates a detail view of the communal hub 34 and the slider 60, with certain components removed for clarity of description and illustration. As illustrated in FIGS. 5 and 5A, in the injection configuration, the slider 60 is in the injection position, where the inner surface of the cap portion 78 of the second portion 71 abuts or mates with the outer surface of the slider portion 41. When the slider 60 is in the injection position, the seal devices 76b in the second portion 71 of the slider 60 are positioned to open a flow path from the injection fluid chamber port 39 to the needle port 42 disposed in the communal hub 34 as indicated by arrow 89, while the seal devices 76a in the first portion 70 of the slider 60 are positioned to block a flow path from the needle port 42 disposed in the communal hub 34 to the withdrawal chamber fluid port 37. For example, as the fluid flows around the slider 60 in the gap D, the seal devices 76b prevent the flow from traversing into the first portion 70 of the slider 60. In this manner, a user can inject fluid, for example, medicant(s), from the injection barrel chamber lumen 19 to the patient when the syringe 10 is in the injection configuration.

In some implementations, the user may initially fill the injectable fluid chamber lumen 19 with fluid, e.g., medicant(s), from a bottle or other source of medicant(s). In some implementations, the injectable fluid chamber lumen 19 may be preloaded with fluid, e.g., medicant(s). The user may then withdraw fluid from the affected joints. For example, the user may position the slider 60 in the withdrawal position and insert the tip 48 of the needle 43 at the affected joints.

Distal movement of the first plunger 25 creates negative relative pressure or vacuum in the withdrawal chamber barrel 12 allowing the user to withdraw fluid from the patient's joint space. The withdrawn fluid will flow into the withdrawal chamber barrel 12. Notably, as the test indicator 65 is positioned in the test indicator chamber 64, the withdrawn fluid may not reach the withdrawal chamber barrel lumen 17. As the fluid contacts the test indicator 65, a chemical reaction between the fluid and a substance (e.g., reagent) carried by the test indicator 65 may provide an indication (e.g., visually perceptible change) of the presence of fluids which are known to be found in joint spaces, such as, for example, bursae, which are filled with synovial fluid. For example, synovial fluids have a high concentration of protein. Again, to test such presence, the test indicator 65 may comprise a reagent strip or other strips which use glucose oxidase, hexokinase, or cupric sulfate, for example, or comprise appropriate chemistry to determine the protein content or presence. The test indicator 65 may indicate presence of protein colorimetrically, which may be read visually or in some implementations through a reflectance photometer.

Once the user confirms that the tip 48 of the needle 43 is correctly positioned in the joint space by detecting a change in the test indicator 65, the user may, for example, depress the cap portion 78 of the second portion 71 of the slider 60 to move the slider 60 to the injection position. The user may then precisely apply the injectable fluid (e.g., an Active Pharmaceutical Agent, such as corticosteroid, hyaluronic acid or a biologic), by proximally moving or depressing the second plunger 30, which will create a positive pressure in the injectable fluid chamber barrel 14, thus expelling the injectable fluid into the joint via the tip 48 of the needle 43.

In addition, to facilitate and/or ease precise direction of flow of fluid, the communal hub 34 may include markings which indicate the direction of flow. For example, the markings may include an inflow mark 90 indicating flow into the withdrawal chamber barrel lumen 17 and an outflow mark 91 indicating flow out of the injection chamber barrel lumen 19. The markings (e.g., 90, 91) may be painted, printed, or etched on the communal hub 34.

Figure 6A:
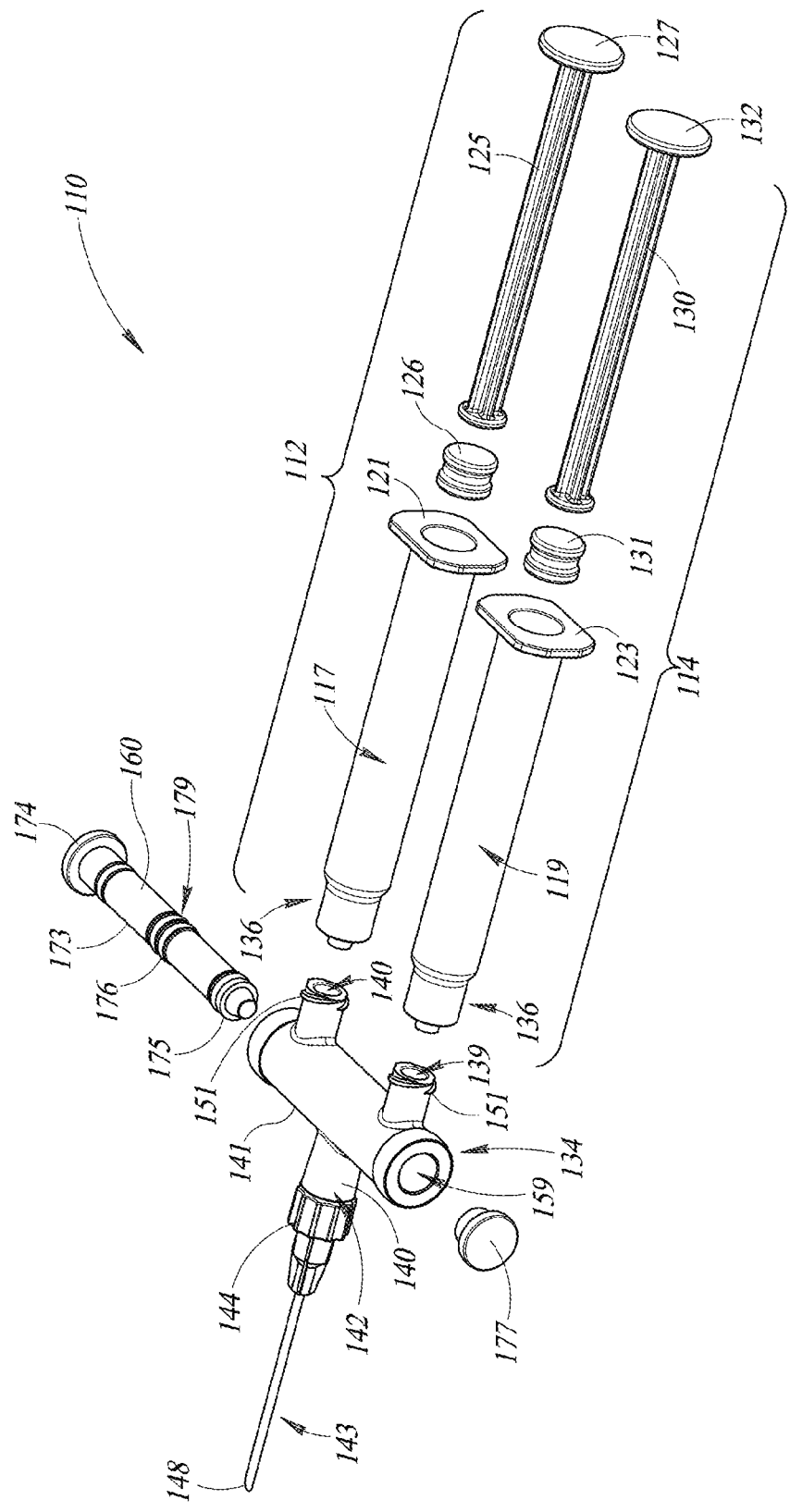
FIG. 6A is an exploded view of a syringe, according to one implementation.
Figure 6B:
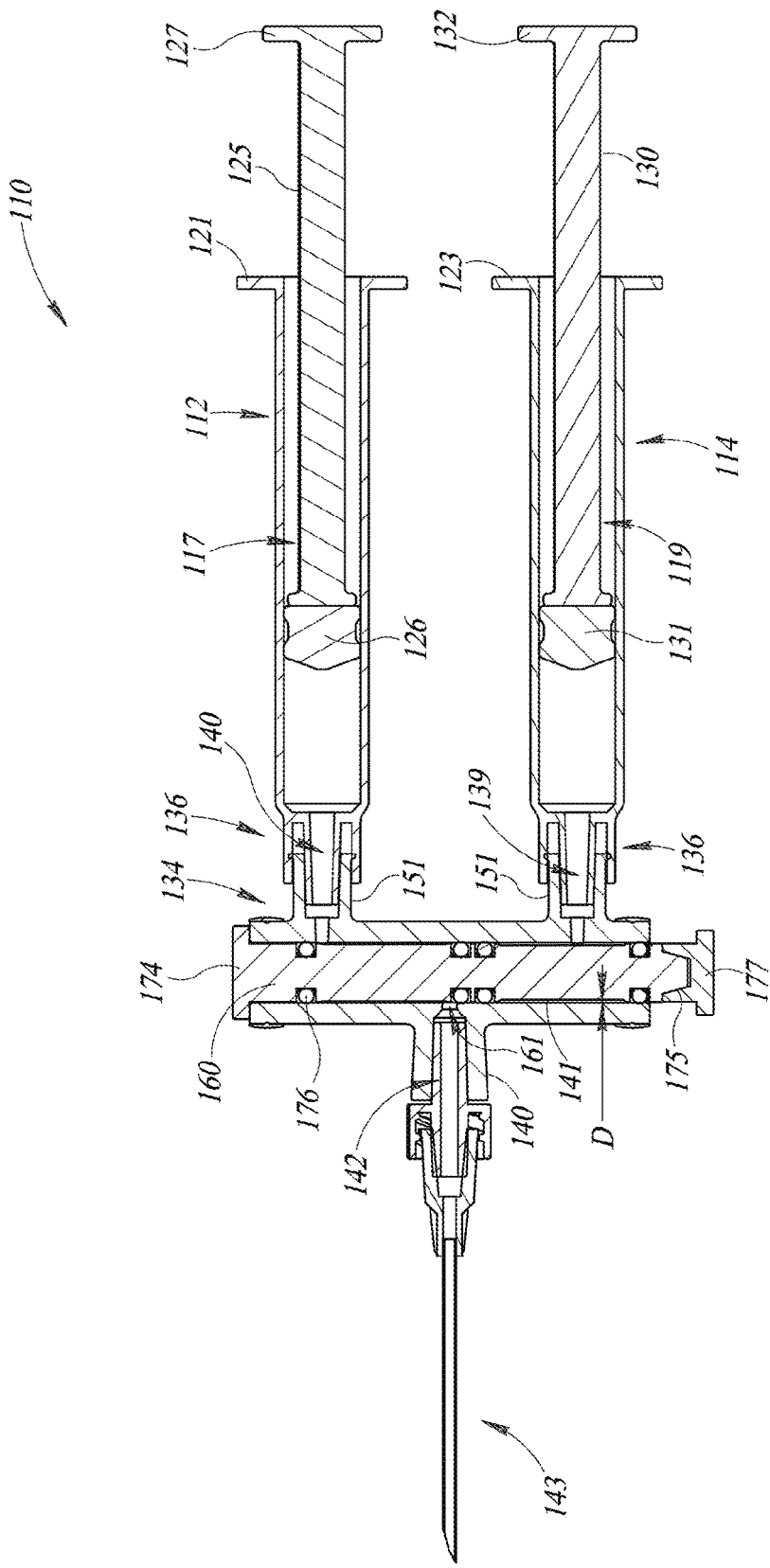
FIG. 6B is a cross-sectional view of the syringe of FIG. 6A, illustrating the syringe in a withdrawal configuration.

In some implementations, a syringe 110, according to an alternate implementation, may omit the test indicator housing 63. For example, FIGS. 6A-B illustrate a variation of the syringe 10 of FIGS. 1-5A which excludes the test indicator housing 63. The syringe 110 includes a withdrawal chamber barrel 112 and an injectable fluid chamber barrel 114. The barrels 112, 114 each have a respective interior space or lumen 117, 119. Again, the withdrawal chamber barrel 112 and the injectable fluid chamber barrel 114 may be formed of transparent or translucent materials, such as clear plastic or glass, to allow a user to view the interior of the withdrawal chamber and injectable fluid chamber barrels 112, 114. In addition, the withdrawal chamber and injectable fluid chamber barrels 112, 114 may include graduation markings to allow the user to view a fluid against the graduation markings to assess the volume of fluid in the respective chamber barrels 112, 114.

An upper end of the withdrawal chamber barrel 112 optionally includes a finger flange 121 that extends peripherally around an upper end of the withdrawal chamber barrel 112. An upper end of the injectable fluid chamber barrel 114 also optionally includes a finger flange 123 that extends peripherally around an upper end of the injectable fluid chamber barrel 114. Again, as discussed above, the finger flange 121 of the withdrawal chamber barrel 112 and the finger flange 123 of the injectable fluid chamber barrel 114 may have various shapes such as cylindrical, hexagonal, square, oval, etc.

The syringe 110 includes a first plunger 125 and a head or plunger seal 126 at a lower end of the first plunger 125. The first plunger 125 is partially received in the withdrawal chamber lumen 117 of the withdrawal chamber barrel 112. The plunger seal 126 sealingly engages with an interior surface of the withdrawal chamber barrel 112 which forms the withdrawal chamber lumen 117.

The first plunger 125 is slideably moveable within the withdrawal chamber barrel 112 and includes a thumb rest 127.

The syringe 110 also includes a second plunger 130 and a head or plunger seal 131 at a lower end of the second plunger 130. The second plunger 130 is partially received in the injectable fluid chamber lumen 119 of the injectable fluid chamber barrel 114. The second plunger 130 is slideably moveable within the injectable fluid chamber barrel 114 and includes a thumb rest 132.

As discussed above, the plunger seals 126, 131 sealingly engage with the interior surfaces of the withdrawal chamber lumen 117 and/or the injectable fluid chamber barrel lumen 119 to create the pressure differentials which allow fluid to be drawn toward the withdrawal chamber barrel lumen 117 and/or the injectable fluid chamber barrel lumen 119 through movement of the corresponding first and/or second plungers 125, 130. Further, as discussed above, proximal movement of second plunger 130 relative to the lower end of the injectable fluid chamber barrel 114 creates a positive pressure to expel the fluid in the injectable fluid chamber barrel lumen 119.

As shown in FIGS. 6A-B, the withdrawal chamber barrel 112 and the injectable fluid chamber barrel 114 are detachably coupleable to a communal hub 134. In particular, the syringe 110 includes coupling adapters 136, for example, in the form of female and male Luer-Lock portions, which directly or indirectly couple the withdrawal chamber and the injectable fluid chamber barrels 112, 114 to the communal hub 134. Female couplers, for example, in the form of female Luer-Lock portions, are located at respective lower ends of the withdrawal chamber barrel 112 and the injectable fluid chamber barrel 114. Male couplers 151, for example, in the form of a male Luer-Lock portion, are located at lower ends of the communal hub 134 proximal to corresponding injectable fluid chamber fluid port 139 and withdrawal chamber barrel fluid port 140. The injectable fluid chamber fluid port 139 and the withdrawal chamber barrel fluid port 140 provide a fluidly communicative path to the injection chamber barrel lumen 119 and the withdrawal chamber barrel lumen 117, respectively. Again, the male Luer-Lock portions are physically detachably coupleable to corresponding female Luer-Lock portions.

The communal hub 134 includes a needle portion 140 and a slider portion 141. The needle portion 140 includes one or more needle ports 142 via which a needle 143 is coupled to the communal hub 134. Again, as discussed above, the one or more needle ports 142 may be formed by or part of a Luer-Lock connector or coupler. The needle 143 includes a needle hub 144 and a needle shaft 147. Again, in some implementations, the needle hub 144 may be integral with the communal hub 134 as a unitary, single piece. The needle shaft 147 includes a beveled end or point or tip 148, and includes a lumen extending therethrough. The needle 143 is fluidly communicatively coupled to the syringe 110 to withdraw or expel fluid when administering to a patient.

The slider portion 141 of the communal hub 134 is substantially cylindrical shaped and hollow, and defines an opening 159 to receive a slider 160. The slider portion 141 includes a first port 161 in fluid communication with the needle port 142 and the withdrawal chamber fluid port 140 and the injectable fluid chamber fluid port 139.

The slider 160, in this implementation, includes a shaft portion 173 extending from a cap portion 174. The cap portion 174 is sized and shaped to have an external outer diameter which is greater than the outer diameter of the shaft portion 173. At a lower end, the shaft portion 173 includes a tapered portion 175 which couples to a coupling cap portion 177. Again, the coupling cap portion 177 has an external outer diameter which is greater than the outer diameter of the shaft portion 173. As discussed above, having the cap portion 174 and the coupling cap portion 177 sized and shaped in this manner allows the cap portion 174 and the coupling cap portion 177 to act as a stop when the slider 161 is moved between its extreme positions and indicate to a user if the syringe 110 is in a withdrawal configuration or an injection configuration.

As shown in FIGS. 6A-B, the shaft portion 173 includes a plurality of slider grooves 179 which extend around a periphery of an outer surface of the shaft portion 173. A first pair of slider grooves 179 are spaced apart in an axial direction and a second pair of slider grooves 179 are spaced apart in the axial direction. The slider grooves 179 are sized and shaped to receive seal devices 176, such as, for example, O-rings. A first pair of seal devices 176 are received in the first pair of slider grooves 179 to provide a first chamber, and a second pair of seal devices 176 are received in the second pair of slider grooves 179 to provide a second chamber. The seal devices 176 are sized and shaped to provide a frictional fit between the shaft portion 173 and an interior surface of the slider portion 141 of the communal hub 134. Again, such frictional forces will at least be higher than the gravitational forces which will prevent the slider 160 from translating due to gravitational forces. Thus, in order to move or translate the slider, a user may depress the cap portion 174 or the coupling cap portion 177 with a force sufficient to overcome the frictional forces provided by the sealing engagement of the seal devices 176 with the interior surface of the slider portion 141.

As discussed above, the slider 160 is disposed in the opening 159 of the communal hub 134. More particularly, the shaft portion 173 is sized and shaped to define a relatively small gap D between an outer surface of the shaft portion 173 and an interior surface of the slider portion 141. As shown in FIGS. 6A-6B, in this manner, the gap D is provided in the first chamber between the first pair of seal devices 176 and in the second chamber between the second pair of seal devices 176. Again, in some implementations, the gap D may have a range of between 100 to 500 microns. In other implementations, the gap D may be sized to provide sufficient area to allow fluid flow while minimizing fluid losses to improve efficiency. In particular, the gap D defines a flow path for the fluid drawn into the communal hub 134 or expelled from the communal hub 134 to flow around the outer surface of the shaft portion 173.

As discussed in more detail above, the slider 160 is disposed in the opening 159 to translate between different positions, e.g., withdrawal, neutral, and/or injection positions, in a direction which is substantially perpendicular to a flow path of fluid drawn into the communal hub 134 via the needle 143 and expelled from the communal hub 134 via the needle 143. For example, FIG. 6B illustrates the slider 160 in the withdrawal position. As discussed above with reference to FIGS. 3, 3A, in this position, the seal devices 176 are positioned to open a flow path from the needle port 142 through the withdrawal chamber barrel fluid port 140 into the withdrawal chamber barrel lumen 117, while closing the flow path to the injection chamber barrel lumen 119 by preventing the flow from traversing the centrally positioned seal devices 176 and entering the injection chamber barrel lumen 119.

Although not shown, the slider 160, similar to the discussion above with reference to FIGS. 4, 4A also can be in a neutral position. In the neutral position, the seal devices 176 are positioned to prevent fluid flow into or out of the injection chamber barrel lumen 119 and the withdrawal chamber barrel lumen 117. In particular, when the syringe 110 is in the neutral position, as the injection chamber barrel lumen 119 and the withdrawal barrel chamber lumen 117 are restricted from receiving any fluid from the needle 143, such prevents or mitigates cross-contamination, as only one of the withdrawal chamber barrel 112 or the injection chamber barrel 114 can be used concurrently.

Although not shown, the slider 160, similar to the discussion above with reference to FIGS. 5A, 5B also can be in an injection position. When the slider 160 is in the injection position, an inner surface of the cap portion 177 abuts or mates with the outer surface of the slider portion 141. Further, in the injection position, the seal devices 176 are positioned to open a flow path from the injection fluid chamber port 139 to the needle port 142, while closing the flow path to the withdrawal chamber barrel lumen 117 by preventing the flow from traversing the centrally positioned seal devices 176 and entering the withdrawal chamber barrel lumen 117.

The various implementations described above can be combined to provide further implementations. All of the U.S. patents, U.S. patent application publications, U.S. patent applications, foreign patents, foreign patent applications and non-patent publications referred to in this specification and/or listed in the Application Data Sheet are incorporated herein by reference, in their entirety, including but not limited to U.S. Ser. No. 14/519,934, filed Oct. 21, 2014, U.S. Patent Application Ser. No. 62/275,422, filed Jan. 6, 2016, U.S. Patent Application Ser. No. 62/326,597, filed Apr. 22, 2016, and U.S. Patent Application Ser. No. 62/401,618, filed Sep. 29, 2016. Aspects of the implementations can be modified, if necessary to employ concepts of the various patents, applications and publications to provide yet further implementations.

Moreover, the various components described herein may advantageously be provided as a kit. The kit may, for example, include a communal hub with a test indicator. The test indicator may include a material with one or more substances (e.g., reagents) that react in a defined manner (e.g., change color) in the presence of defined substances. The communal hub may include a mechanism, such as, for example, the various implementations of the slider described herein, that are operable to selectively provide one or more fluidly communicative paths. The communal hub may include adapters such that the communal hub is coupleable to a needle and chamber barrels. The kit may also include withdrawal chamber and injectable fluid chamber barrels to precisely confirm and administer injectable fluids to the affected areas. Alternatively, the kit may only include a communal hub, test indicator, and a withdrawal chamber barrel. The injectable fluid barrel may be supplied by the user. The kit may also include injectable fluids or medicant(s) that are being administered at the affected areas and needles. The kit may also include a set of instructions for effective use of the syringe.

Furthermore, a method to use the various implementations of the syringes described herein may include filling an injectable fluid chamber lumen of an injectable fluid chamber barrel with a medicant(s). The injectable fluid chamber barrel may then be coupled to a communal hub, according to one or more implementations of the communal hubs described herein, via coupling adapters, for example, Luer Locks. The method may include coupling an empty withdrawal chamber barrel to the communal hub via coupling adapters, for example, Luer Locks. A plunger of the withdrawal chamber barrel may be in a fully or at least partially depressed position. The method may include coupling a needle to the communal hub via, for example, Luer Locks.

The method may further include inserting a needle into bodily tissue of a patient, for example, at intra-articular locations. The method may include withdrawing the plunger of the withdrawal chamber barrel to draw fluid from the patient, for example, synovial fluid, so the fluid is drawn into a chamber disposed in the communal hub that houses a test indicator. The operator of the syringe may wait to observe if the test indicator responds in a defined manner. In some implementations, if no response is observed the operator may remove and discard the withdrawal chamber barrel and couple another withdrawal chamber barrel. In some implementations, the operator may continue manipulating the syringe until a response of the test indicator is observed.

Once a response of the test indicator is observed, the operator may depress the slider to move the slider to the injection position. The operator may thereafter depress the plunger of the injectable fluid chamber barrel to inject the medicant(s). The method may further include removing the syringe from the patient. In some implementations, the removed syringe may be discarded or disposed.

These and other changes can be made to the implementations in light of the above-detailed description. In general, in the following claims, the terms used should not be construed to limit the claims to the specific implementations disclosed in the specification and the claims, but should be construed to include all possible implementations along with the full scope of equivalents to which such claims are entitled. Accordingly, the claims are not limited by the disclosure.

The invention claimed is:

1. A syringe, comprising:
a first barrel having an interior surface that forms a first barrel lumen;
a first plunger having a head, the head of the first plunger slideably received in the first barrel lumen for movement therein, the head of the first plunger in sealing engagement with the interior surface of the first barrel;
a second barrel having an interior surface that forms a second barrel lumen;
a second plunger having a head, the head of the second plunger slideably received in the second barrel lumen for movement therein, the head of the second plunger in sealing engagement with the interior surface of the second barrel;
a hub having an orifice, the hub which provides a first fluidly communicative path between the orifice of the hub and the first barrel lumen and a second fluidly communicative path between the orifice of the hub and the second barrel lumen, at least a portion of the first and the second fluidly communicative paths which extend parallel to one another;
a slider slideably received via the hub and translatable along an axis that is perpendicular to at least the portions of the first and the second fluidly communicative paths which extend parallel to one another, between a first configuration and a second configuration, the slider in the first configuration opens the first fluidly communicative path between the orifice of the hub and the first barrel lumen and closes the second fluidly communicative path between the orifice of the hub and the second barrel lumen, and the slider in the second configuration opens the second fluidly communicative path between the orifice of the hub and the second barrel lumen and closes the first fluidly communicative path between the orifice of the hub and the first barrel lumen, the slider having:
  a first external surface spaced apart from an internal surface of the hub by a first gap; and
  a second external surface spaced apart from the internal surface of the hub by a second gap;
a plurality of seals sealingly received around the slider, wherein at least a first pair of spaced apart seals of the plurality of seals are sealingly coupled to the first external surface and at least a second pair of spaced apart seals of the plurality of seals are sealingly coupled to the second external surface, the first pair of spaced apart seals arranged to open the first fluidly communicative path between the orifice of the hub and the first barrel lumen via the first gap while the second gap is fluidly blocked by the second pair of spaced apart seals when the slider is in the first configuration, and the second pair of spaced apart seals are arranged to open the second fluidly communicative path between the orifice of the hub and the second barrel lumen via the second gap while the first gap is fluidly blocked by the first pair of spaced apart seals when the slider is in the second configuration; and
a test indicator responsive to at least one characteristic of bodily fluid, the test indicator positioned to be exposed to any bodily fluid drawn into the first barrel lumen and visible from an exterior of the first barrel.

2. The syringe of claim 1 wherein the hub includes an opening through which the slider slideably translates between the first and the second configurations.

3. The syringe of claim 1, further comprising:
  a test indicator housing coupled to the first barrel lumen; and
  a one-way valve disposed in the test indicator housing which allows flow of bodily fluid into the first barrel lumen and which prevents flow of bodily fluid out of the first barrel lumen to the hub.

4. The syringe of claim 1 wherein the hub includes a first port and a second port, the first port and the second port fluidly communicatively coupling the orifice of the hub to the first barrel lumen when the slider is in the first configuration.

5. The syringe of claim 4 wherein the hub includes a third port, the first port and the third port fluidly communicatively coupling the orifice of the hub to the second barrel lumen when the slider is in the second configuration.

6. The syringe of claim 1 wherein the hub includes a first port, a second port, and a third port, the slider alternatively communicatively coupling the orifice of the hub to the first barrel lumen via the first port and the second port in the first configuration and the orifice of the hub to the second barrel lumen via the first port and the third port in the second configuration.

7. The syringe of claim 1 wherein the slider includes a pair of opposed cap portions which extend from the hub at locations which are diametrically opposed to one another across the hub.

8. The syringe of claim 7 wherein a first one of the pair of opposed cap portions mates with the hub to prevent downward translation of the slider when in the first configuration, and a second one of the pair of opposed cap portions mates with the hub to prevent upward translation of the slider when in the second configuration.

9. The syringe of claim 1, wherein the first pair of spaced apart seals are positioned to sealingly engage the hub and block bodily fluid flowing to the first barrel lumen from entering the second barrel lumen when the slider is in the first configuration, and at least the second pair of spaced apart seals are positioned to sealingly engage the hub and block injectable fluid flowing from the second barrel lumen from entering the first barrel lumen when the slider is in the second configuration.

10. The syringe of claim 1, further comprising:
  a needle adapter coupleable to the hub; and
  a needle having a shaft, the shaft coupled to the needle adapter at one end thereof and the shaft having a bevel at another end thereof.

11. The syringe of claim 10 wherein the needle adapter and the hub are integrally formed as a unitary piece.

12. A syringe, comprising:
  a first barrel having an interior surface that forms a first barrel lumen which receives bodily fluid;
  a first plunger having a head, the head of the first plunger slideably received in the first barrel lumen for movement therein, the head of the first plunger in sealing engagement with the interior surface of the first barrel;
  a second barrel having an interior surface that forms a second barrel lumen which holds an injectable fluid;
  a second plunger having a head, the head of the second plunger slideably received in the second barrel lumen for movement therein, the head of the second plunger in sealing engagement with the interior surface of the second barrel;
  a hub having an orifice through which bodily fluid is drawn into the first barrel lumen and the injectable fluid is expelled from the second barrel lumen;
  a slider having an exterior surface which translates between a first position and a second position in a direction which is perpendicular to a flow path of the bodily fluid drawn into the hub, the exterior surface of the slider exposed to the bodily fluid when the bodily fluid is drawn into the hub and the exterior surface of the slider exposed to the injectable fluid when the injectable fluid is expelled from the hub, the slider in the first position opens a fluidly communicative path between the orifice of the hub and the first barrel lumen and closes a fluidly communicative path between the orifice of the hub and the second barrel lumen, and the slider in the second position opens a fluidly communicative path between the orifice of the hub and the second barrel lumen and closes the fluidly communicative path between the orifice of the hub and the first barrel lumen; wherein:
    the exterior surface is spaced apart from an interior surface of the hub by a first gap to define a first chamber; and
    the exterior surface is spaced apart from the interior surface of the hub by a second gap to define a second chamber;
  a plurality of seals sealingly received around the slider, wherein at least a first pair of spaced apart seals of the plurality of seals are sealingly coupled to the exterior surface at opposing ends of the first chamber, and at least a second pair of spaced apart seals of the plurality of seals are sealingly coupled to the exterior surface at opposing ends of the second chamber, the first pair of seals arranged to open the fluidly communicative path between the orifice of the hub and the first barrel lumen via the first chamber while the second pair of spaced apart seals are arranged to close the fluidly communicative path between the orifice of the hub and the second barrel lumen when the slider is in the first position, and the second pair of seals arranged to open the fluidly communicative path between the orifice of the hub and the second barrel lumen via the second chamber while the first pair of seals are arranged to close the fluidly communicative path between the orifice of the hub and the first barrel lumen when the slider is in the second position; and a test indicator responsive to at least one characteristic of the bodily fluid, the test indicator positioned to be exposed to any bodily fluid drawn into the first barrel lumen and visible from an exterior of the first barrel.

13. The syringe of claim 12 wherein the hub includes an opening through which the slider translates between the first and the second positions.

14. The syringe of claim 12, further comprising:
a test indicator housing coupled to the first barrel lumen; and
a one-way valve disposed in the test indicator housing which allows flow of bodily fluid into the first barrel lumen and which prevents flow of bodily fluid out of the first barrel lumen to the hub.

15. The syringe of claim 12 wherein the hub includes a first port and a second port, the first port and the second port fluidly communicatively coupling the orifice of the hub to the first barrel lumen when the slider is in the first position.

16. The syringe of claim 15 wherein the hub includes a third port, the first port and the third port fluidly communicatively coupling the orifice of the hub to the second barrel lumen when the slider is in the second position.

17. The syringe of claim 12 wherein the hub includes a first port, a second port, and a third port, the slider alternatively communicatively coupling the orifice of the hub to the first barrel lumen via the first port and the second port in the first position and the orifice of the hub to the second barrel lumen via the first port and the third port in the second position.

18. The syringe of claim 12, wherein the first pair of spaced apart seals are positioned to sealingly engage the hub and block bodily fluid flowing to the first barrel lumen from entering the second barrel lumen when the slider is in the first position, and the second pair of spaced apart seals are positioned to sealingly engage the hub and block injectable fluid flowing from the second barrel lumen from entering the first barrel lumen when the slider is in the second position.

19. The syringe of claim 12, further comprising:
a needle adapter coupleable to the hub; and
a needle having a shaft, the shaft coupled to the needle adapter at one end thereof and the shaft having a bevel at another end thereof.

20. The syringe of claim 12 wherein the slider includes a pair of end caps which are located across the hub at locations diametrically opposed to one another.

21. A syringe, comprising:
a first barrel having an interior surface that forms a first barrel lumen;
a first plunger having a head, the head of the first plunger slideably received in the first barrel lumen for movement therein, the head of the first plunger in sealing engagement with the interior surface of the first barrel;
a second barrel having an interior surface that forms a second barrel lumen;
a second plunger having a head, the head of the second plunger slideably received in the second barrel lumen for movement therein, the head of the second plunger in sealing engagement with the interior surface of the second barrel;
a hub having an orifice, the hub which provides a first fluidly communicative path between the orifice of the hub and the first barrel lumen and a second fluidly communicative path between the orifice of the hub and the second barrel lumen, at least a portion of the first and the second fluidly communicative paths which extend parallel to one another;
a slider slideably received via the hub and translatable along an axis that is perpendicular to at least the portions of the first and the second fluidly communicative paths which extend parallel to one another, between a first configuration and a second configuration, the slider in the first configuration opens the first fluidly communicative path between the orifice of the hub and the first barrel lumen and closes the second fluidly communicative path between the orifice of the hub and the second barrel lumen, and the slider in the second configuration opens the second fluidly communicative path between the orifice of the hub and the second barrel lumen and closes the first fluidly communicative path between the orifice of the hub and the first barrel lumen, the slider having:
a first external surface spaced apart from an internal surface of the hub by a first gap; and
a second external surface spaced apart from the internal surface of the hub by a second gap; and
a plurality of seals sealingly received around the slider, wherein at least a first pair of spaced apart seals of the plurality of seals are sealingly coupled to the first external surface and at least a second pair of spaced apart seals of the plurality of seals are sealingly coupled to the second external surface, the first pair of spaced apart seals arranged to open the first fluidly communicative path between the orifice of the hub and the first barrel lumen via the first gap while the second gap is fluidly blocked by the second pair of spaced apart seals when the slider is in the first configuration, and the second pair of spaced apart seals are arranged to open the second fluidly communicative path between the orifice of the hub and the second barrel lumen via the second gap while the first gap is fluidly blocked by the first pair of spaced apart seals when the slider is in the second configuration.

22. The syringe of claim 21 wherein the hub includes an opening through which the slider slideably translates between the first and the second configurations.

23. The syringe of claim 21 wherein the hub includes a first port and a second port, the first port and the second port fluidly communicatively coupling the orifice of the hub to the first barrel lumen when the slider is in the first configuration.

24. The syringe of claim 23 wherein the hub includes a third port, the first port and the third port fluidly communicatively coupling the orifice of the hub to the second barrel lumen when the slider is in the second configuration.

25. The syringe of claim 21 wherein the hub includes a first port, a second port, and a third port, the slider alternatively communicatively coupling the orifice of the hub to the first barrel lumen via the first port and the second port in the first configuration and the orifice of the hub to the second barrel lumen via the first port and the third port in the second configuration.

26. The syringe of claim 21 wherein the slider includes a pair of opposed cap portions which extend from the hub at locations which are diametrically opposed to one another across the hub.

27. The syringe of claim 26 wherein a first one of the pair of opposed cap portions mates with the hub to prevent downward translation of the slider when in the first configuration, and a second one of the pair of opposed cap portions mates with the hub to prevent upward translation of the slider when in the second configuration.

28. The syringe of claim 21, wherein the first pair of spaced apart seals are positioned to sealingly engage the hub and block bodily fluid flowing to the first barrel lumen from entering the second barrel lumen when the slider is in the first configuration, and the second pair of spaced apart seals are positioned to sealingly engage the hub and block injectable fluid flowing from the second barrel lumen from entering the first barrel lumen when the slider is in the second configuration.

29. A syringe, comprising:
a first barrel having an interior surface that forms a first barrel lumen which receives bodily fluid;
a first plunger having a head, the head of the first plunger slideably received in the first barrel lumen for movement therein, the head of the first plunger in sealing engagement with the interior surface of the first barrel;
a second barrel having an interior surface that forms a second barrel lumen which holds an injectable fluid;
a second plunger having a head, the head of the second plunger slideably received in the second barrel lumen for movement therein, the head of the second plunger in sealing engagement with the interior surface of the second barrel;
a hub having an orifice through which bodily fluid is drawn into the first barrel lumen and the injectable fluid is expelled from the second barrel lumen; and
a slider having:
an exterior surface which translates between a first position and a second position in a direction which is perpendicular to a flow path of the bodily fluid drawn into the hub, the exterior surface of the slider exposed to the bodily fluid when the bodily fluid is drawn into the hub and the exterior surface of the slider exposed to the injectable fluid when the injectable fluid is expelled from the hub, the slider in the first position opens a fluidly communicative path between the orifice of the hub and the first barrel lumen and closes a fluidly communicative path between the orifice of the hub and the second barrel lumen, and the slider in the second position opens a fluidly communicative path between the orifice of the hub and the second barrel lumen and closes the fluidly communicative path between the orifice of the hub and the first barrel lumen; wherein:
the exterior surface is spaced apart from an interior surface of the hub by a first gap to define a first chamber; and
the exterior surface is spaced apart from the interior surface of the hub by a second gap to define a second chamber; and
a plurality of seals sealingly received around the slider, wherein at least a first pair of spaced apart seals of the plurality of seals are sealingly coupled to the exterior surface at opposing ends of the first chamber, and at least a second pair of spaced apart seals of the plurality of seals are sealingly coupled to the exterior surface at opposing ends of the second chamber, the first pair of seals arranged to open the fluidly communicative path between the orifice of the hub and the first barrel lumen via the first chamber while the second pair of spaced apart seals are arranged to close the fluidly communicative path between the orifice of the hub and the second barrel lumen when the slider is in the first position, and the second pair of seals arranged to open the fluidly communicative path between the orifice of the hub and the second barrel lumen via the second chamber while the first pair of seals are arranged to close the fluidly communicative path between the orifice of the hub and the first barrel lumen when the slider is in the second position.

30. The syringe of claim 29 wherein the hub includes an opening through which the slider translates between the first and the second positions.

31. The syringe of claim 29 wherein the hub includes a first port and a second port, the first port and the second port fluidly communicatively coupling the orifice of the hub to the first barrel lumen when the slider is in the first position.

32. The syringe of claim 31 wherein the hub includes a third port, the first port and the third port fluidly communicatively coupling the orifice of the hub to the second barrel lumen when the slider is in the second position.

33. The syringe of claim 29 wherein the hub includes a first port, a second port, and a third port, the slider alternatively communicatively coupling the orifice of the hub to the first barrel lumen via the first port and the second port in the first position and the orifice of the hub to the second barrel lumen via the first port and the third port in the second position.

34. The syringe of claim 29, wherein the first pair of spaced apart seals are positioned to sealingly engage the hub and block bodily fluid flowing to the first barrel lumen from entering the second barrel lumen when the slider is in the first position, and the second pair of spaced apart seals which are positioned to sealingly engage the hub and block injectable fluid flowing from the second barrel lumen from entering the first barrel lumen when the slider is in the second position.

35. The syringe of claim 29, further comprising:
a needle adapter coupleable to the hub; and
a needle having a shaft, the shaft coupled to the needle adapter at one end thereof and the shaft having a bevel at another end thereof.

36. The syringe of claim 29 wherein the slider includes a pair of end caps which are located across the hub at locations diametrically opposed to one another.

37. A syringe, comprising:
a first barrel having an interior surface that forms a first barrel lumen;
a first plunger having a head, the head of the first plunger slideably received in the first barrel lumen for movement therein, the head of the first plunger in sealing engagement with the interior surface of the first barrel;
a second barrel having an interior surface that forms a second barrel lumen;
a second plunger having a head, the head of the second plunger slideably received in the second barrel lumen for movement therein, the head of the second plunger in sealing engagement with the interior surface of the second barrel;
a hub having an orifice, the hub which provides a first fluidly communicative path between the orifice of the hub and the first barrel lumen and a second fluidly communicative path between the orifice of the hub and the second barrel lumen;

a needle hub coupleable to the hub, the needle hub having a needle lumen, the needle hub which provides a third fluidly communicative path between the needle lumen and the hub;

a slider slideably received via the hub and translatable along an axis that is perpendicular to the third fluidly communicative path, between a first configuration and a second configuration, the slider having:
- a first external surface spaced apart from an internal surface of the hub by a first gap; and
- a second external surface spaced apart from the internal surface of the hub by a second gap;

a first pair of spaced apart seals that are sealingly coupled to the first external surface; and a second pair of spaced apart seals that are sealingly coupled to the second external surface, the first pair of spaced apart seals are arranged to open the first fluidly communicative path between the orifice of the hub and the first barrel lumen via the first gap while the second pair of spaced apart seals are arranged to close the second fluidly communicative path between the orifice of the hub and the second barrel lumen when the slider is in the first configuration, and the second pair of spaced apart seals are arranged to open the second fluidly communicative path between the orifice of the hub and the second barrel lumen via the second gap while the first pair of spaced apart seals are arranged to close the first fluidly communicative path between the orifice of the hub and the first barrel lumen when the slider is in the second configuration.

* * * * *